(12) United States Patent
Zhong et al.

(10) Patent No.: US 12,139,752 B2
(45) Date of Patent: Nov. 12, 2024

(54) METHODS FOR RNA SEQUENCING

(71) Applicant: GENEMO INC., San Diego, CA (US)

(72) Inventors: Sheng Zhong, San Diego, CA (US); Zixu Zhou, San Diego, CA (US)

(73) Assignee: GENEMO INC., San Diego, CA (US)

( * ) Notice: Subject to any disclaimer, the term of this patent is extended or adjusted under 35 U.S.C. 154(b) by 623 days.

(21) Appl. No.: 16/798,837

(22) Filed: Feb. 24, 2020

(65) Prior Publication Data

US 2020/0291465 A1  Sep. 17, 2020

Related U.S. Application Data

(63) Continuation of application No. PCT/US2018/032959, filed on May 16, 2018.

(60) Provisional application No. 62/553,691, filed on Sep. 1, 2017.

(51) Int. Cl.
    *C12Q 1/6844* (2018.01)
    *C40B 40/08* (2006.01)
    *C40B 50/06* (2006.01)

(52) U.S. Cl.
    CPC .... *C12Q 1/6846* (2013.01); *C12Y 302/02027* (2013.01); *C40B 40/08* (2013.01); *C40B 50/06* (2013.01)

(58) Field of Classification Search
    CPC .......... C09K 8/52; C09K 8/524; C09K 8/582; C09K 8/584; C09K 8/60; C09K 2208/32; C12N 1/16; C12N 1/18; C12N 1/20; C12N 1/6806; C12N 1/6844; C12N 1/6846; C12N 1/6869; C12Q 1/6806; C12Q 1/6844; C12Q 1/6846; C12Q 1/6869; C12Q 2521/107; C12Q 2521/501; C12Q 2521/531; C12Q 2525/191; C12Q 2535/122; C12Q 2525/205; C12Y 302/02027; C40B 40/08; C40B 50/06
    See application file for complete search history.

(56) References Cited

U.S. PATENT DOCUMENTS

| | | |
|---|---|---|
| 2005/0003440 A1 | 1/2005 | Kopreski |
| 2015/0176073 A1* | 6/2015 | Skog ................ C12Q 1/702 435/6.12 |
| 2015/0299767 A1* | 10/2015 | Armour ............ C12Q 1/6844 506/26 |
| 2016/0053315 A1* | 2/2016 | Soldatov ........... C12Q 1/6848 435/6.12 |
| 2016/0122756 A1 | 5/2016 | Armour |

FOREIGN PATENT DOCUMENTS

| | | |
|---|---|---|
| WO | 2015195780 A1 | 12/2015 |
| WO | 2016109799 A2 | 7/2016 |

OTHER PUBLICATIONS

Rinchai et al. (F1000Research 2017, 5:1385, Mar. 10, 2017, 19 pages).*

(Continued)

*Primary Examiner* — Jeremy C Flinders
(74) *Attorney, Agent, or Firm* — METIS IP LLC

(57) ABSTRACT

This invention provides methods for detecting RNAs in a biological sample while using only a small amount of sample input, e.g., less than or equal to 1 mL. The methods described herein are able to detect a large percentage of protein-coding genes having the ENSEMBL gene annotation HG38.

26 Claims, 2 Drawing Sheets

(56) References Cited

OTHER PUBLICATIONS

Saurabh Agarwal et al., Sequencing of First-Strand cDNA Library Reveals Full-Length Transcriptomes, Nature Communications, 6: 1-12, 2015.
Joshua Z Levin et al., Comprehensive Comparative Analysis of Strand-Specific RNA Sequencing Methods, Nature Methods, 2010, 10 pages.
International Search Report in PCT/US2018/032959 mailed on Jul. 23, 2018, 4 pages.
Written Opinion in PCT/US2018/032959 mailed on Jul. 23, 2018, 8 pages.

* cited by examiner

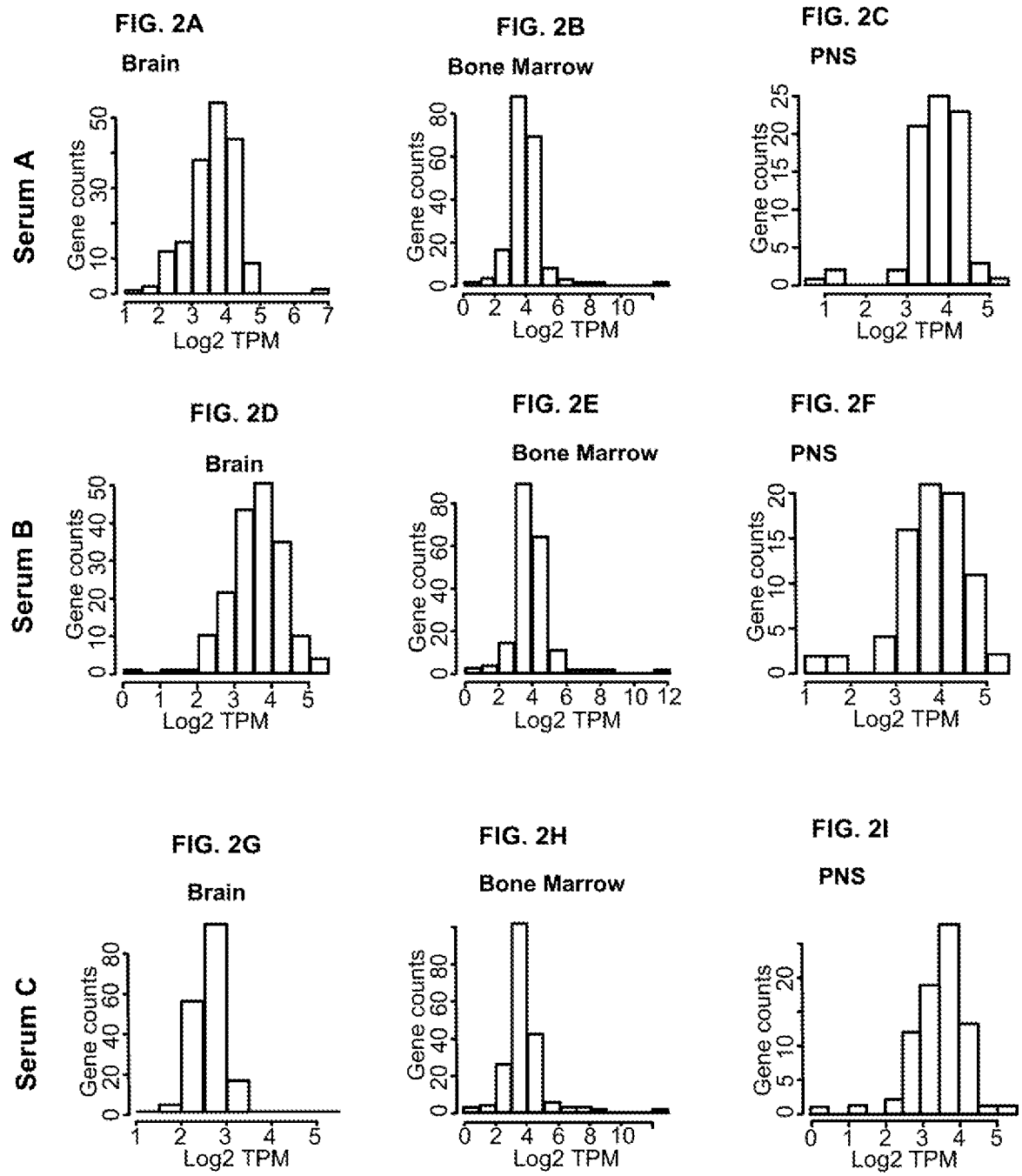

METHODS FOR RNA SEQUENCING

CROSS-REFERENCE TO RELATED APPLICATIONS

This application is a continuation of PCT/US2018/032959, filed May 16, 2018, which application claims priority to U.S. Provisional Application No. 62/553,691, filed Sep. 1, 2017, the disclosures of which are hereby incorporated by reference in their entireties for all purposes.

FIELD OF THE INVENTION

The invention relates to the field of nucleic acid sequencing and library construction.

BACKGROUND

While nucleic acid molecules encode valuable information about a subject's genetic makeup and disease conditions, sequencing nucleic acid molecules, especially ribonucleic acids (RNAs), has been challenging. Traditional RNA sequencing methods often require a large amount of biological sample to obtain enough RNAs for downstream sequencing and/or library construction. The isolation and purification of RNAs from the sample is a complicated and time consuming process that often requires the use of multiple reagents, prolonged periods of protein precipitation and washing, and sometimes exposure to high temperature and high salt solutions. In addition to the multistep process, the RNAs may undergo degradation or unwanted modification, making downstream sequencing reactions less accurate. There exists a need for novel and efficient methods to sequencing RNAs from biological samples.

SUMMARY OF THE INVENTION

This invention provides methods for detecting RNAs in a biological sample (e.g., a cell-free biological sample) while using only a small amount of sample input, e.g., less than or equal to 1 mL. Depending on the biological sample, in some embodiments, the methods described herein may detect at least about 100 different genes. As demonstrated in Examples 1-3, the methods detected a large percentage of protein-coding genes having the ENSEMBL gene annotation HG38.

In one aspect, the invention provides a method for detecting a plurality of ribonucleic acids (RNAs) in a biological sample from a subject by (a) constructing a cDNA library from the plurality of RNAs in the biological sample, wherein an effective volume of the biological sample used to construct the cDNA library is less than or equal to about 1 mL; and (b) detecting RNA genome equivalents in the cDNA library.

In some embodiments, the effective volume of the biological sample is less than or equal to about 500 μL (e.g., less than or equal to about 250 μL, less than or equal to about 100 μL, less than or equal to about 50 μL, less than or equal to about 25 μL, or less than or equal to about 10 μL). In other embodiments, the effective volume of the biological sample is between about 1 μL and about 500 μL (e.g., between about 1 μL and about 250 μL, between about 1 μL and about 100 μL, between about 1 μL and about 50 μL, between about 1 μL and about 25 μL, between about 1 μL and about 10 μL, between about 5 μL and about 100 μL, between about 5 μL and about 50 μL, between about 5 μL and about 25 μL, between about 5 μL and about 10 μL, between about 10 μL and about 100 μL, between about 10 μL and about 50 μL, between about 10 μL and about 25 μL, between about 25 μL and about 100 μL, between about 25 μL and about 50 μL, or between about 50 μL and about 100 μL).

In some embodiments, the biological sample is a cell-free biological sample.

In some embodiments, at least about 100 different genes (e.g., at least about 1,000 different genes, at least about 5,000 different genes, at least about 10,000 different genes, at least about 20,000 different genes, at least about 30,000 different genes, at least about 40,000 different genes, or at least about 50,000 different genes) are detected. In some embodiments, the different genes comprise different categories of RNAs (e.g., mRNA, lincRNA, miRNA, snRNA, and combinations thereof).

In some embodiments, the biological sample is a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample. In particular embodiments, the biological sample is a serum sample, a plasma sample, a saliva sample, or a cell culture media sample. In particular embodiments, the cell culture media sample is a serum sample or a plasma sample. In particular embodiments, the cell culture media sample is an in vitro fertilization (IVF) culture media sample.

In some embodiments, step (a) of the method comprises: (a1) breaking up lipid bilayers and/or ribonucleoprotein complexes in the biological sample; (a2) removing deoxyribonucleic acids (DNAs) in the biological sample; (a3) synthesizing a plurality of short, double-stranded complementary DNAs (cDNAs) oligonucleotides using the RNAs in the biological sample as templates; (a4) ligating at least one adaptor to an end of each short, double-stranded cDNA oligonucleotide to generate a plurality of adaptor-ligated, double-stranded cDNA oligonucleotides; (a5) amplifying the plurality of adaptor-ligated, double-stranded cDNA oligonucleotides using primers that hybridize to the adaptor; (a6) selecting one strand of each adaptor-ligated, double-stranded cDNA oligonucleotide; and (a7) amplifying the selected strand of each adaptor-ligated, double-stranded cDNA oligonucleotide to generate the cDNA library, wherein the cDNA library comprises cDNA oligonucleotides having the same sequences as the sequences of the genomic DNAs from which the RNAs are transcribed.

In some embodiments, step (a4) described above comprises ligating two adaptors each to one end of each short, double-stranded cDNA oligonucleotide to generate a plurality of adaptor-ligated, double-stranded cDNA oligonucleotides. In particular embodiments, the two adaptors are the same. In particular embodiments, the two adaptors are different. In some embodiments, one of the adaptors comprises a degradable sequence. In particular embodiments, the degradable sequence comprises a uracil DNA glycosylase recognition sequence.

In some embodiments, step (a3) described above comprises: (a3.1) synthesizing a plurality of first strand cDNAs by reverse transcribing the RNAs in the biological sample; (a3.2) fragmenting the plurality of first strand cDNAs to generate a plurality of cDNA fragments; (a3.3) ligating a 3' primer to the 3' end of each cDNA fragment in the plurality of cDNA fragments; and (a3.4) synthesizing the plurality of short, double-stranded cDNA oligonucleotides using a targeting primer and the plurality of cDNA fragments as templates, wherein the targeting primer comprises a first portion comprising a sequence complementary to the sequence of the 3' primer and a second portion comprising a degradable sequence. In particular embodiments, the degradable sequence comprises a uracil DNA glycosylase recognition sequence. In particular embodiments, the 3' primer is an oligonucleotide comprising identical nucleotides (e.g., a poly(G) oligonucleotide, a poly(C) oligonucleotide, a poly(A) oligonucleotide, a poly(T) oligonucleotide, or a poly(U) oligonucleotide). In particular embodiments, the 3' primer is a poly(G) oligonucleotide. In particular embodiments, the sequence of the first portion is a poly(C) oligonucleotide.

In some embodiments, the method further comprises removing the RNAs in the biological sample. The RNAs may be removed using a metal ion and/or heat shock.

In some embodiments of the method, the plurality of adaptor-ligated, double-stranded cDNA oligonucleotides is purified using a charge-based purification method prior to step (a5) described above. In particular embodiments, the charge-based purification method comprises using beads.

In particular embodiments, in step (a6) described above, the strand comprising the adaptor that comprises the degradable sequence is degraded. In some embodiments, the strand is degraded by a uracil DNA glycosylase.

In some embodiments of the method, the method further comprises removing cDNA oligonucleotides that encode ribosomal RNAs (rRNAs) after step (a6) and prior to step (a7). In particular embodiments, an rRNA primer is used to target the cDNA oligonucleotides encoding rRNAs.

In some embodiments of the method, step (b) comprises: (b1) sequencing the cDNA library to detect the RNA genome equivalents. The methods described herein may generate any number of sequencing reads. In particular embodiments, at least about 1,000 sequencing reads (e.g., at least about 5,000 sequencing reads, at least about 10,000 sequencing reads, at least about 50,000 sequencing reads, at least about 100,000 sequencing reads, at least about 500,000 sequencing reads, at least about 1 million sequencing reads, at least about 1.5 million sequencing reads, at least about 2 million sequencing reads, at least about 2.5 million sequencing reads, at least about 5 million sequencing reads, at least about 10 million sequencing reads, at least about 25 million sequencing reads, or at least about 50 million sequencing reads) are obtained. In some embodiments, step (b) further comprises: (b2) mapping the RNA genome equivalents detected to different categories of RNAs.

Other inventive products, methods, and features that can be used alone or in combination with the aforesaid methods are evidenced by the description and examples that follow.

BRIEF DESCRIPTION OF THE DRAWINGS

FIGS. 2A-2I are bar graphs showing the distribution of the TPM (transcripts per million) values of genes specific to each of the three tissues in serum A (FIGS. 2A-2C), serum B (FIGS. 2D-2F), and serum C (FIGS. 2G-2I).

DETAILED DESCRIPTION OF THE INVENTION

I. Introduction

Figure 1:
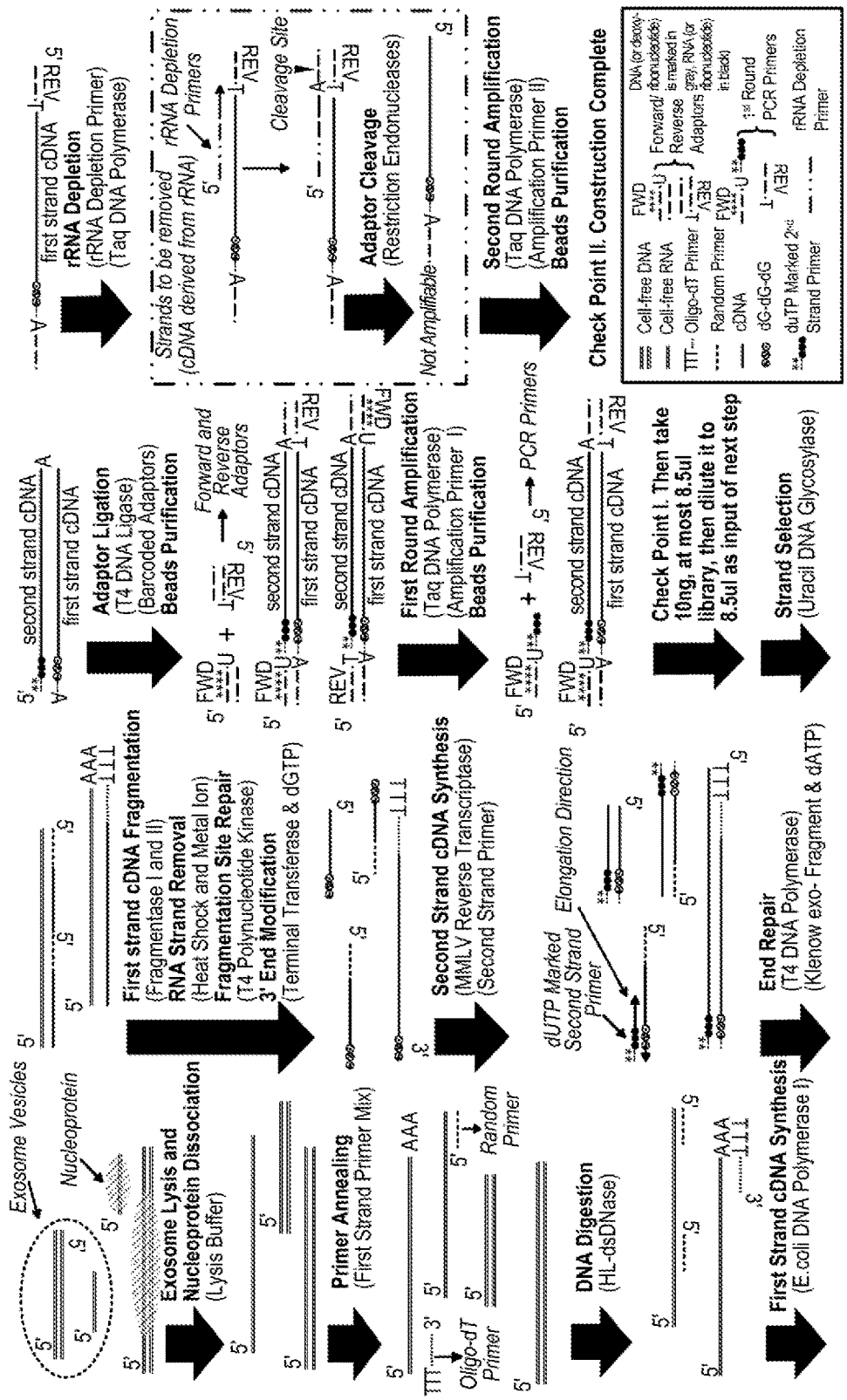
FIG. 1 is an exemplary schematic flowchart showing non-limiting steps in the method of the invention.

The invention features a technology that is able to construct sequencing libraries in large scale with small amounts of biological sample such as unprocessed serum as the direct input. Using a small amount of biological sample (e.g., a cell-free biological sample) such as unprocessed serum, the technology may allow the detection of at least 100 different genes. For example, as demonstrated in Examples 1-3, with about 60 µL of unprocessed serum, we detected over 50,000 out of all 60,675 human genes among 42 different gene categories (ENSEMBL gene annotation (HG38)). Further, we were also able to detect tissue-specific genes in serum. The technology could be applied to different liquid biopsy types, such as saliva and in vitro fertilization (IVF) culture media, for the diagnosis and prognosis of various diseases.

II. Definitions

As used herein, the term "biological sample" refers to a biological sample obtained from a subject that can either be directly used in the methods of the invention or be processed before being used in the methods of the invention. Examples of a biological sample from a subject include, but are not limited to, a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, and a stool sample. In some embodiments, a biological sample may be a cell-free biological sample, which refers to a biological sample obtained from a subject (e.g., a human) that does not contain any cells or is subsequently processed to remove substantially all of the cells present in the sample. For example, a whole blood sample from a subject may be filtered to remove cells, e.g., red blood cells, white blood cells, and platelets. In some embodiments, a cell-free biological sample may also be constructed from a biological material obtained from a subject. For example, during IVF, a mature egg may be collected from the subject and fertilized by sperm in a laboratory. The cell culture media used to culture the fertilized egg is an example of a cell-free biological sample.

As used herein, the term "effective volume" refers to the volume of the biological sample (e.g., a cell-free biological sample) that may allow the detection of at least about 100 different genes in the biological sample. For example, if 5 biological samples each containing 10 µL are used to construct 5 cDNA libraries and the sequencing reads from each cDNA library are about 6 million for a total of about 30 million sequencing reads (6 million×5 samples), then the effective volume of the biological sample is 50 µL (10 µL×5 samples). In another example, if one 50 µL biological sample is sequenced 5 times, in which the sequencing reads each time are about 6 million for a total of 30 million sequencing reads after 5 times, then the effective volume of the biological sample is 50 µL.

As used herein, the term "RNA genome equivalent" refers to the sequence of the RNA that is amplified in the cDNA library constructed based on the RNAs present in the biological sample (e.g., a cell-free biological sample). The cDNA library is then sequenced to detect the RNA genome equivalents, thus, detecting the RNAs present in the original biological sample.

As used herein, the term "genomic DNA" refers to the DNA from which the RNAs are transcribed. The term "genomic DNA" does not refer to DNAs that may present in the biological sample (e.g., a cell-free biological sample). Genomic DNA is DNA that constitutes the genome of the organism.

As used herein, the term "cDNA" or "complementary DNA" refers to a DNA oligonucleotide synthesized from an RNA template either directly or in subsequent amplifications. A cDNA oligonucleotide may be generated using an RNA as the template in a reaction catalyzed by the enzyme reverse transcriptase. This cDNA oligonucleotide may further be used as the template to synthesis other cDNA oligonucleotides, e.g., a second cDNA oligonucleotide generated based on a first cDNA oligonucleotide as the template. As described in detail herein, double-stranded cDNA oligonucleotides containing a first strand cDNA oligonucleotide (generated based on the RNAs in the biological sample (e.g., a cell-free biological sample) as the template) and a second cDNA oligonucleotide (generated based on the first strand cDNA oligonucleotide as the template) are made prior to adaptor ligation. Eventually, the second strand cDNA oligonucleotides are targeted for degradation and the first strand cDNA oligonucleotides are selected for the second stage of PCR amplification to construct the cDNA library. Note that the sequences of the first cDNA oligonucleotides are the same as the sequences of the genomic DNAs that are used to generate the RNAs in the biological sample. Note that the sequences of the second cDNA oligonucleotides are the same as the sequences of the RNAs, except that the uracils are replaced with thymidines.

As used herein, the term "gene" refers to a component of an organism's genome that is made of deoxyribonucleic acids (DNAs) and/or ribonucleic acids (RNAs). A gene may be a coding gene, which encodes the genetic sequence of a protein or peptide that is eventually expressed after gene transcription and translation. A gene may be a non-coding gene, which encodes a genetic sequence that may not be expressed into a protein or peptide and serves other functions in the organism's genome, such as regulating the expression of other genes.

As used herein, the term "lipid bilayers" refers to any cell membranes or vesicle membranes. Cell membranes or vesicle membranes may enclose a cell, enclose a vesicle, or present inside a cell or a vesicle. For example, lipid bilayers may be the outer membrane of a cell. In other embodiments, lipid bilayers may be the membrane of a vesicle, e.g., an exosome.

As used herein, the term "adaptor" refers to short, double-stranded oligonucleotides that are ligated to the ends of double-stranded cDNA oligonucleotides before the first stage of PCR amplification. The primers used during the first stage of PCR amplification may be designed to anneal to the adaptors in a manner such that only one type of ligation product is amplified. As described in detail further herein, a forward adaptor may include a degradable sequence (e.g., a uracil DNA glycosylase recognition sequence (e.g., a sequence containing dUTP)), which can be recognized by a uracil DNA glycosylase during downstream strand selection and degradation.

As used herein, the term "degradable sequence" refers to any nucleotide sequence that can be recognized by a protein, which then targets the oligonucleotide containing the degradable sequence for degradation. For example, the enzyme uracil DNA glycosylase recognizes a sequence containing dUTP (e.g., a uracil DNA glycosylase recognition sequence) and targets the oligonucleotide containing such a sequence for degradation.

As used herein, the term "3' primer" refers to a short oligonucleotide that is ligated to the 3' end of each cDNA fragment before the synthesis of the second strand cDNA oligonucleotides. In some embodiments, a 3' primer comprises identical nucleotides (e.g., a poly(G) oligonucleotide, a poly(C) oligonucleotide, a poly(A) oligonucleotide, a poly(T) oligonucleotide, or a poly(U) oligonucleotide).

As used herein, the term "charge based nucleotide purification method" refers to a method for nucleotide purification that relies on the interactions between the oligonucleotide and the solid phase based on their charges. In some embodiments, a charge based nucleotide purification method may use silica based columns or silica coated beads (e.g., silica coated magnetic beads).

As used herein, the term "about" refers to a range of values that is ±20% of the specific value. For example, "about 30 million" includes ±20% of 30 million, or from 24 million to 36 million. When the specific value is a percentage, the upper limit is 100%. Thus, about 95% refers to from 75% to 100%. Such a range performs the desired function or achieves the desired result. For example, "about" may refer to an amount that is within less than 20% of, less than 10% of, within less than 5% of, within less than 1% of, within less than 0.1% of, and within less than 0.01% of the specific value.

As used herein, the term "between" refers to any quantity within the range indicated and enclosing each of the ends of the range indicated. For example, between 50 µL and 100 µL refers to any quantity within 50 µL and 100 µL, as well as 50 µL and 100 µL. The term "between about," e.g., between about 50 µL and about 100 µL, refers to any quantity within the range indicated and enclosing 50 µL−(50 µL×20%) as the lower bound and 100 µL+(100 µL×20%) as the upper bound. For example, "between about 50 µL and about 100 µL" refers to from 40 µL to 120 µL.

As used herein, the term "subject," "individual," and "patient" are used interchangeably herein to refer to a vertebrate, preferably a mammal, more preferably a human. Mammals include, but are not limited to, mice, murines, rats, simians, humans, farm animals, sport animals, and pets.

III. Membrane Lysis and RNA Isolation

In certain aspects, the methods of the invention include a first step of breaking up membranes, exosomes, and/or ribonucleoprotein complexes in the biological sample (e.g., a cell-free biological sample). A biological sample that may be used to analyze and sequence RNAs using methods described herein may be, or may be derived from, a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample. In some embodiments, the above-mentioned samples may be used directly as the biological sample in the methods. In other embodiments, the above-mentioned samples may undergo a process to remove cells present in the samples in order to acquire cell-free biological samples to be used in the methods. For example, a whole blood sample may be processed to remove cells, e.g., white blood cells and red blood cells, to obtain a cell-free biological sample. Methods and devices used for separating or removing cells from a biological sample are known in the art and include, but are not limited to, plateletpheresis, sedimentation, and centrifugation.

A biological sample (e.g., a cell-free biological sample) may be lysed to break up membranes, exosomes, and/or ribonucleoprotein complexes. In some embodiments, RNAs often exist in complex with proteins or in exosomes to be protected from RNase degradation. Exosomes are cell-derived vesicles that are present in biological samples. Exosomes may be released from the cell when multivesicular bodies fuse with the plasma membrane or released directly from the plasma membrane. The molecular components in exosomes include, e.g., RNAs, DNAs, and proteins. Ribonucleoprotein complexes are protein complexes that contain RNAs, e.g., protein-RNA complexes. For example, RNAs that may be complexed with proteins include, but are not limited to, lincRNAs (long intergenic noncoding RNAs), miRNAs (microRNAs), and snRNAs (small nuclear RNAs). A biological sample (e.g., a cell-free biological sample) may be lysed using a lysis buffer to break up membranes and exosomes and dissociate ribonucleoprotein complexes. A lysis buffer may be any aqueous solution that is capable of breaking open or lysing the membranes, exosomes, and/or ribonucleoprotein complexes in the biological sample (e.g., a cell-free biological sample) to release the RNAs into the solution without degrading, fragmenting, or modifying the RNAs. In some embodiments, a lysis buffer used in the methods of the invention may include, e.g., one or more detergents (e.g., NP-40), one or more proteases, one or more RNase inhibitors (e.g., a solution containing between about 5% w/v and about 15% w/v SDS (e.g., about 6% w/v, about 8% w/v, about 10% w/v, about 12% w/v, or about 14% w/v SDS; e.g., about 10% w/v SDS)), one or more redox agents (e.g., a DTT (dithiothreitol) solution), one or more salts, one or more buffering agents, and/or one or more chelating agents. A lysis buffer may also be adjusted to or kept at a desired pH range (e.g., a pH of between 6 and 8 (e.g., a pH of 6, 6.2, 6.4, 6.6, 6.8, 7, 7.2, 7.4, 7.6, 7.8, or 8, such as a pH of 7.4) for the most efficient lysis and to provide a stable environment for the RNAs. Furthermore, depending on the type of biological sample, the detergents, proteases, RNase inhibitors, salts, buffering agents, chelating agents, and their respective amounts and concentrations in the lysis buffer may be tailored to the specific biological sample. The components of the lysis buffer described herein may be provided in admixture or separately added to the biological sample to form the lysis solution.

The biological sample (e.g., a cell-free biological sample) may be contacted with a lysis buffer to form a lysis solution. In some embodiments, the lysis solution may be mixed and incubated at room temperature for about 1 minute to about 10 minutes (e.g., about 1, 2, 3, 4, 5, 6, 7, 8, 9, or 10 minutes; e.g., about 5 minutes) for efficient membrane and exosome lysis and ribonucleoprotein complex dissociation. In other embodiments, the lysis solution may be mixed and incubated in a heated environment at, e.g., between about 50° C. and about 60° C. (e.g., about 51° C., 52° C., 53° C., 54° C., 55° C., 56° C., 57° C., 58° C., or 59° C.; e.g., about 55° C.) for about 1 minute to about 10 minutes (e.g., about 1, 2, 3, 4, 5, 6, 7, 8, 9, or 10 minutes; e.g., about 5 minutes) for efficient membrane and exosome lysis and ribonucleoprotein complex dissociation, provided that the heated environment does not degrade the RNAs.

Detergents in the lysis buffer enable the disruption and solublization of membranes, exosomes, and proteins. Detergents are amphipathic molecules containing both a nonpolar tail group having aliphatic or aromatic character and a polar head group. Detergents in the lysis buffer may be nonionic, anionic, cationic, zwitterionic, or a mixture thereof. Examples of detergents that may be included in a lysis buffer used in methods of the invention include, but are not limited to, NP-40, Triton X 100, Triton X-114, Tween 20 (polysorbate 20), Tween 40, Tween 60, Tween 80, 3 [(3 cholamidopropyl)dimethylammonio]-1-propanesulfonate (CHAPS), 3 [(3 cholamidopropyl)-dimethylammonio]-2-hydroxy-1-propanesulfonate (CHAPSO), octyl glucoside, octyl thioglucoside, bile salts (e.g., cholate), and quaternary ammonium surfactants (e.g., cetyl trimethyl ammonium bromide (CTAB), tetradecyl trimethyl ammonium bromide (TTAB), ethyl trimethyl ammonium bromide (ETAB)). In some embodiments, the detergent in the lysis buffer is NP-40. The amount of detergent in a lysis buffer may be optimized by one of skill in the art. In some embodiments, the lysis buffer contains between 0.01% and 10% (e.g., about 0.025%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%; e.g., about 4%) of a detergent (e.g., NP-40).

In some embodiments, the lysis buffer used in the methods of the invention may include one or more proteases. A protease is an enzyme that breaks down proteins into smaller peptides and amino acids by proteolysis. Proteases may be classified according to the catalytic group involved in its active site. Examples of classes of proteases include, but are not limited to, serine proteases (e.g., proteinase K, chymotrypsin, trypsin, elastase, plasmin, thrombin, acrosomal protease, complement C1, keratinase, collagenase, fibrinolysin, and cocoonase), cysteine proteases (e.g., papain, bromelain, cathepsin, calpain, caspase-1, sortase, TEV protease, and hepatitis C virus peptidase 2), threonine proteases, aspartic proteases, glutamic proteases, metalloproteases, and asparagine peptide lyases. In some embodiments of the methods described herein, the lysis buffer includes a serine protease (e.g., proteinase K).

The lysis solution may further contain a buffering agent to prevent a rapid change in pH of the solution. Examples of a buffering agent include, but are not limited to, tris(hydroxymethyl)aminomethane (Tris), citric acid, acetic acid, potassium phosphate, borate, N-Cyclohexyl-2-aminoethanesulfonic acid (CHES), tris(hydroxymethyl)methylaminopropanesulfonic acid (TAPS), bicine, tricine, 3-(N-Tris-(hydroxymethyl)methylamino)-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 3-(N-morpholino)propanesulfonic acid (MOPS), piperazine-N,N'-bis (2-ethanesulfonic acid (PIPES), cacodylate, and 2-(N-morpholino)ethanesulfonic acid (MES). In some embodiments, the buffering agent in the lysis buffer is Tris. A buffering agent may maintain the pH of the lysis buffer at a pH of between 6 and 8 (e.g., a pH of 6, 6.2, 6.4, 6.6, 6.8, 7, 7.2, 7.4, 7.6, 7.8, or 8, such as a pH of 7.4) for the most efficient membrane, exosome, and ribonucleoprotein complex lysis and dissociation and to provide a stable environment for the isolated RNAs. The lysis buffer used in methods of the invention may also contain additional reagents, such as chelating agents, reducing agents, stabilizers, organic or inorganic salts, metal ions, and/or pH indicators. A chelating agent, such as ethylenediaminetetraacetic acid (EDTA), may be included in the lysis buffer (e.g., as Tris-EDTA, known also as TE buffer).

Following membrane and exosome lysis and ribonucleoprotein complex dissociation, the sample may be processed to capture the RNAs by primer annealing. A primer mixture containing, e.g., poly(T) primers (e.g., TTTTTT) that can hybridize to the poly(A) tail of the RNAs and a plurality of random primers (e.g., primers having six nucleotides; e.g., hexamers), may be added to the sample to anneal to the RNAs. The conditions for primer annealing may be tailored based on the length of the primers and the biological sample by one of skill in the art. For example, the sample may be incubated with the primer mix at about 70° C. for about 2 minutes for the primers to anneal to the RNAs.

Further, the sample may be processed to remove DNAs present in the sample. A DNase (e.g., DNase I or DNase II) may be added to the sample to degrade DNAs by catalyzing the hydrolytic cleavage of phosphodiester linkages in the DNA backbone, thus degrading the DNAs. In some embodiments, the DNase used in the methods described herein is DNase I. In particular embodiments, an RNase inhibitor may be pre-mixed with a DNase-containing reagent and mixture may be added to the sample. An RNase inhibitor may be a protein or small molecule compound used to inhibit RNA degradation by RNase. In particular embodiments, the RNase inhibitor is a protein that binds to certain classes of ribonucleases (e.g., an RNase inhibitor that inhibits RNases A, B, and C). In some embodiments, the RNase inhibitor is a small molecule compound.

For example, a mixture containing a DNase-containing reagent and an RNase inhibitor may be added to the sample after membrane and exosome lysis and ribonucleoprotein complex dissociation. The resulting mixture may be mixed and incubated at, e.g., 37° C. and/or 65° C., for a few minutes, e.g., 5-10 minutes, for the enzymatic DNA degradation, e.g., by DNase I, to take place (e.g., incubation at 37° C. for 10 minutes followed by 65° C. for 5 minutes). In some embodiments, a higher incubation temperature (e.g., 65° C.) may be used to deactivate the DNase and/or the RNase inhibitor.

IV. Reverse-Transcription of RNAs to cDNAs

First Strand cDNA Synthesis

A complementary DNA (cDNA) is a DNA oligonucleotide synthesized from an RNA template in a reaction catalyzed by the enzyme reverse transcriptase. In some embodiments, a cDNA oligonucleotide also refers to a second DNA oligonucleotide generated based on a first cDNA oligonucleotide as the template. A reverse transcriptase operates on a single-stranded RNA and generates its cDNA based on the pairing of RNA base pairs (e.g., adenine, guanine, cytosine, and uracil) to their DNA complements (e.g., thymine, cytosine, guanine, and adenine, respectively). The sample containing the RNAs annealed with the primers as described above is used to synthesize the first strand cDNA. For example, a mixture containing a DNA polymerase I (e.g., an E. coli DNA polymerase I) and in some embodiments, also an RNase inhibitor (e.g., a protein that inhibits RNases A, B, and C) may be added to the sample, so the DNA polymerase I can use the RNA as a template and synthesize the cDNA by adding nucleotides to the 3' end of the primers that are annealed to the RNA. The DNA polymerase I eventually generates a RNA-cDNA hybrid. The reaction conditions used to generate the RNA-cDNA hybrid may be designed and adjusted by one of skill in the art based on, e.g., the length of the RNA template, the type of biological sample, and the concentration of the RNAs. For example, a thermocycler programmed to, e.g., 25° C. for 10 minutes, 40° C. for 5 minutes, and 70° C. for 10 minutes, may be used to generate the RNA-cDNA hybrid.

First Strand cDNA Processing and RNA Removal

Once the RNA-cDNA hybrids are generated in the sample, the hybrids may be fragmented to shorter strands and the RNA portion may be removed. Enzymes such as fragmentases may be used to generate shorter RNA-cDNA strands. For example, a two-enzyme system including two fragmentases may be used, in which one fragmentase generates single-strand nicks on one strand of the RNA-cDNA hybrid and the other fragmentase cuts the other strand at locations corresponding to the nicks. The fragmentation reaction may be performed by adding the two fragmentases to the sample and incubating the sample at, e.g., 37° C. for about 30 minutes. The resulting products are short RNA-cDNA hybrids. Following the fragmentation reaction, the RNA portion of the hybrids may be degraded by adding a buffer rich in high metal ion (e.g., a buffer containing a high concentration of $Zn^{2+}$) in combination with heat shock (e.g., heating at 90° C. for about 2 minutes). In other embodiments, the RNA portion of the hybrids may be degraded by adding an RNase to the sample. Subsequent to RNA degradation, normal ionic strength of the sample may be restored by adding a chelating agent, such as ethylenediaminetetraacetic acid (EDTA), which can effectively bind to the metal ions (e.g., $Zn^{2+}$) used during RNA degradation.

After the RNAs are degraded, the sample now contains first strand cDNA fragments. To ensure that each cDNA fragment contains a 5' phosphate and a 3' hydroxyl, a T4 polynucleotide kinase may be added to the sample to repair the cDNA fragments. The T4 polynucleotide kinase catalyzes the transfer of a γ-phosphate from ATP to the 5' hydroxyl end of the cDNA fragments, thus, adding a 5' phosphate to the cDNA fragment. Further, a 3' primer (e.g., a poly(G) (e.g., GGG) portion) may be added to the 3' end of the cDNA fragments using a terminal transferase, which a specialized DNA polymerase that catalyzes the addition of nucleotides to the 3' end of a DNA molecule. A terminal transferase does not require a template to perform the reaction. At this stage, a plurality of short cDNA oligonucleotides each containing a 3' primer (e.g., a 3' poly(G) portion (e.g., GGG)) is present in the sample.

Second Strand cDNA Synthesis

Each cDNA fragment containing a 3' primer (e.g., a 3' poly(G) portion (e.g., GGG)) may be used as a template to generate a second strand cDNA oligonucleotide. Note that the sequences of the second cDNA oligonucleotides are the same as the sequences of the RNAs, except that the uracils are replaced with thymidines. Also note that the sequences of the first cDNA oligonucleotides are the same as the sequences of the genomic DNAs, from which the RNAs are transcribed. In some embodiments, to generate the second strand cDNA oligonucleotide, the sample may be incubated with a primer that contains two parts: (1) a degradable sequence (e.g., a uracil DNA glycosylase recognition sequence) and (2) a sequence complementary to the sequence of the 3' primer (e.g., a poly(C) sequence (e.g., CCC)), as well as a reverse transcriptase (e.g., a MMLV (moloney murine leukemia virus) reverse transcriptase). The part (2) of the primer (e.g., the poly(C) sequence (e.g., CCC)) may hybridize with the 3' primer (e.g., the 3' poly(G) portion (e.g., GGG)) on each of the first cDNA oligonucleotides. In some embodiments, the synthesis of the second strand cDNAs may proceed in two directions. In one instance, the MMLV reverse transcriptase may use the first cDNA oligonucleotide as a template to generate the second cDNA oligonucleotide. In another instance, the MMLV reverse transcriptase may use the primer (e.g., the primer containing the degradable sequence (e.g., the uracil DNA glycosylase recognition sequence) and the sequence complementary to the sequence of the 3' primer (e.g., the poly(C) sequence (e.g., CCC))) as the template to further elongate the first cDNA oligonucleotide. As shown in FIG. 1, when the MMLV uses the primer as the template, the first cDNA oligonucleotide gets elongated at the 3' end by the addition of a sequence that is complementary to the degradable sequence (e.g., the uracil DNA glycosylase recognition sequence) of the primer. At this stage, the sample contains a plurality of short, double-stranded cDNA oligonucleotides. Moreover, a T4 DNA polymerase may be added to the sample to remove any 3' end overhangs in the double-stranded cDNA oligonucleotides by elongating the shorter strand to create a blunt 3' end in each double-stranded cDNA oligonucleotide. Further, a Klenow-exo fragment enzyme may be added to the sample to ligate an adenine to the 3' end of each strand of the double-stranded cDNA oligonucleotides. As shown in FIG. 1, at this stage, the sample contains a plurality of short, double-stranded cDNA oligonucleotides, in which each double-stranded cDNA oligonucleotides contains an adenine at the 3' end of each strand.

V. Adaptor Ligation, PCR Amplification, and Strand Selection

Each short, double-stranded cDNA oligonucleotide is additionally ligated with at least one adaptor. In some embodiments, each short, double-stranded cDNA oligonucleotide is additionally ligated with two adaptors, one adaptor at each end of the oligonucleotide. In some embodiments, the two adaptors may be the same. In other embodiments, the two adaptors may be different. As shown in FIG. 1, each short, double-stranded cDNA oligonucleotide is additionally ligated with a forward adaptor and a reverse adaptor. As shown in FIG. 1, the forward adaptor may include a degradable sequence (e.g., a uracil DNA glycosylase recognition sequence) that can be recognized by a uracil DNA glycosylase and a 3' uracil overhang that specifically anneals to the 3' adenine on the first strand cDNA oligonucleotide. The reverse adaptor may include a 3' thymine overhang that specifically anneals to the 3' adenine on the second strand cDNA oligonucleotide. The 3' uracil overhang of the forward adaptor and the 3' thymine overhang of the reverse adaptor may allow specific strand selection downstream. As shown in FIG. 1, the desired ligation includes the forward adaptor being ligated to the 5' end of the second strand cDNA oligonucleotide and the reverse adaptor being ligated to the 5' end of the first strand cDNA oligonucleotide. One undesired ligation includes the forward adaptor being ligated to the 5' of the first strand cDNA oligonucleotide and the reverse adaptor being ligated to the 5' end of the second strand cDNA oligonucleotide. In some embodiments, the undesired ligation product, which may be a double-stranded cDNA oligonucleotide having the degradable sequence (e.g., the uracil DNA glycosylase recognition sequence) on both ends, may not be recognized during the downstream PCR amplification reaction. Thus, only the short, double-stranded cDNA oligonucleotides having different 5' and 3' ends may be amplified.

After adaptor ligation, the sample containing the adaptor-ligated, double-stranded cDNA oligonucleotides may be purified using various charge based nucleotide purification methods, such as solid-phase separation methods, e.g., chromatography. Purification of the sample removes undesired materials from the previous steps, e.g., any proteins either from the original biological sample or added during sample processing and nucleic acid debris (e.g., degraded RNAs and DNAs), before the adaptor-ligated, double-stranded cDNA oligonucleotides undergo PCR amplification and subsequent sequencing. Many available charge based nucleotide purification methods rely on the interactions between the oligonucleotide and the solid phase based on their charges. In some embodiments, a charge based nucleotide purification method may use silica based columns or silica coated beads (e.g., silica coated magnetic beads). For example, solid-phase separation methods utilize the attractive interactions between nucleic acid molecules and silica surfaces under optional salt concentrations and pH. In some embodiments, the sample may be mixed with beads, such as magnetic beads coated with silica on their surfaces. Once the adaptor-ligated, double-stranded cDNA oligonucleotides bind to the magnetic beads, the beads can be separated from the aqueous solution using a magnetic separator. The isolated adaptor-ligated, double-stranded cDNA oligonucleotides can subsequently be eluted from the magnetic beads using water or buffered water (e.g., tris-acetate buffered water). The ratio of nucleic acids to magnetic beads may be optimized to improve nucleic acid yield. Magnetic beads designed to isolate nucleic acids are described in, e.g., Smith et al., *J. Clin. Microbiol.*, 41:2440-2443, 2003, Miszczak et al., *J. Clin. Microbiol.*, 49:3694-3696, 2011, and Yang et al., *J. Virol. Methods,* 171:195-199, 2011. Various magnetic beads are also commercially available, e.g., AMPure® beads, MagJET® beads, and Magesil Blue® beads. In other embodiments, the sample may be loaded onto a column containing silica as the solid phase. The supernatant can be removed either by gravity or centrifugation (in the case of spin-columns). The isolated adaptor-ligated, double-stranded cDNA oligonucleotides can then be eluted from the column using water or buffered water (e.g., tris-acetate buffered water).

The purified sample may undergo a first stage of PCR amplification. As shown in FIG. 1, during the first stage of PCR amplification, the forward and reverse primers are designed such that only the adaptor-ligated, double-stranded cDNA oligonucleotides from the desired adaptor ligation reaction may be amplified. Further to the first stage of PCR amplification, the PCR product may be purified using magnetic beads (e.g., AMPure® beads). The PCR product contains double-stranded cDNA oligonucleotides in which the strand having the degradable sequence (e.g., the uracil DNA glycosylase recognition sequence) at the 5' end (e.g., the second strand cDNA oligonucleotide) may be degraded by the enzyme uracil DNA glycosylase. The remaining strand has the sequence of the first strand cDNA oligonucleotide, which is also the sequence of the genomic DNA used to transcribe the RNA, and is thus selected to undergo a second stage of PCR amplification.

Prior the second stage of PCR amplification, cDNA oligonucleotides having the sequences of ribosomal RNAs (rRNAs) may be removed using an rRNA primer that anneals specifically to cDNA oligonucleotides that are derived from rRNAs. Once these cDNA oligonucleotides are amplified using a Taq DNA polymerase, an endonuclease cleavage site integrated in the reverse adaptor is exposed. Using specific endonucleases, the reverse adaptor may be cleaved to render the resulting double-stranded cDNA unable to undergo further rounds of PCR amplification. Examples of endonucleases include, but are not limited to, EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI. Thus, at this stage, the sample contains cDNA oligonucleotides having the same sequences as those of the genomic DNAs and is free of any cDNA oligonucleotides corresponding to rRNAs. Another round of PCR amplification followed by purification on magnetic beads generate a cDNA library that is ready for sequencing.

VI. Sequencing and Genome Mapping

The cDNA library generated from the RNAs may be sequenced to detect various RNA genome equivalents that were present in the original biological sample. The cDNA library may be sequenced using any available sequencing techniques. For example, sequencing methods include classical polymerase-mediated enzymatic methods such as Sanger dideoxy sequencing, as well as capillary based implementations of Sanger sequencing and automated implementations of Sanger sequencing. These commercially available systems for Sanger sequencing include, e.g., 1-Capillary Sequencers, 4-Capillary Sequencers, 16-Capillary Sequencers, 48-Capillary Sequencers, 96-Capillary Sequencers, and the ABI Prism® 3700 series DNA analyzers. Many sequencing approaches include an in vitro cloning step to generate many copies of each individual molecule.

For example, in emulsion PCR individual nucleic acid molecules are isolated along with primer-coated beads in aqueous bubbles within an oil phase. A polymerase chain reaction (PCR) then coats each bead with clonal copies of the isolated library molecule and these beads are subsequently immobilized for later sequencing. In other cases, surface methods of clonal amplification have been developed, for example, by the use of bridge PCR where fragments are amplified upon primers attached to a solid surface. These methods produce many physically isolated locations which each contain many copies of a single fragment. Next-generation sequencing methods may also be used to sequence the cDNA library. Examples of next-generation sequencing methods include, but are not limited to, single-molecule real-time sequencing, ion semiconductor sequencing, pyrosequencing, sequencing by synthesis, sequencing by bridge amplification, sequencing by ligation, nanopore sequencing, chain termination sequencing, massively parallel signature sequencing, polony sequencing, heliscope single molecule sequencing, and oligonucleotide extension sequencing. Various sequencing technologies are described in, e.g., Goodwin et al., *Nature Review Genetics* 17:333, 2016; Buermans and Dunnen, *Biochim. Biophys. Acta* 1842: 1932, 2014; Heather and Chain, *Genomics* 107:1, 2016; and Levy and Myers, *Annu. Rev. Genom. Hum. Genet.* 17:95, 2016, which are all incorporated by reference herein.

The methods described herein may also include subjecting the cDNA library to digital counting and analysis. The number of amplified sequences for each transcript in the amplified sample can be quantitated through sequence reads (e.g., one read per amplified strand). Quantitation during sequencing may allow for the detection and quantitation for each transcript present in the biological sample (e.g., a cell-free biological sample) containing RNAs. The methods described herein use only a small amount of biological sample (e.g., less than or equal to about 1 mL) to obtain sequencing reads that can be used to detect the RNA genome equivalents present in the biological sample, as well as mapping the RNA genome equivalents to different categories of RNAs.

Once the cDNA library is sequenced, the sequences may be mapped to their RNA genome equivalents. Various gene mapping and sequence alignment tools and databases are available, e.g., BLAST, FASTA, Genoogle, HMMER, USEARCH, ScalaBlast, and Genome Compiler. Each tool or database may be tailored to the specific goals of the gene mapping, e.g., filters may be set to search within the genes belonging to a particular tissue or organ, as well as the length of the target gene pool. Gene annotations may also be set to search within the genome of a particular organism or species (e.g., ENSEMBL gene annotation HG38). As demonstrated in Examples 1-3, using only 45 µL of the cell-free biological sample as input, the methods of the invention are able to detect 95% of protein-coding genes having ENSEMBL gene annotation HG38 (e.g., lincRNA, miRNA, and snRNA) and 176 tissue-specific genes for the brain, bone marrow, and the peripheral nervous system (PNS). Depending on the biological sample, in some embodiments, the methods described herein may detect at least about 100 different genes while using less than or equal to about 1 mL (e.g., less than or equal to about 500 µL, less than or equal to about 250 µL, less than or equal to about 100 µL, less than or equal to about 75 µL, less than or equal to about 50 µL, less than or equal to about 25 µL, less than or equal to about 20 µL, less than or equal to about 15 µL, or less than or equal to about 10 µL) of the biological sample. Categories of RNAs that may be detected using methods of the invention include, but are not limited to, lincRNAs, miRNAs, snRNAs, ncRNAs, nmRNAs, sRNAs, smnRNAs, tRNAs, mRNAs, pcRNAs, rRNAs, 5S rRNAs, 5.8S rRNAs, SSU rRNAs, LSU rRNAs, NoRC RNAs, pRNAs, 6S RNAs, SsrS RNAs, aRNAs, asRNAs, asmiRNAs, crRNAs, tracrRNAs, DD RNAs, diRNAs, dsRNAs, endo-siRNAs, exRNAs, gRNAs, hc-siRNAs, hcsiRNAs, hnRNAs, RNAi, lncRNAs, mrpRNAs, nat-siRNAs, natsiRNAs, OxyS RNAs, piRNAs, qiRNAs, rasiRNAs, scaRNAs, scnRNAs, scRNAs, scRNAs, SgrS RNAs, shRNAs, siRNAs, SL RNAs, SmY RNAs, snoRNAs, snRNP, RP RNAs, ssRNAs, stRNAs, tasiRNAs, tmRNAs, uRNAs, vRNAs, vtRNAs, Xist RNAs, Y RNAs, pre-mRNAs, and circRNAs (e.g., lincRNAs, miRNAs, and snRNAs).

VII. Devices

In some embodiments, one or more steps of constructing a cDNA library and detecting the RNA genome equivalents in the cDNA library may be automated using one or more automated sample handling devices (e.g., one or more automated liquid or fluid handling devices). Automated devices and procedures may be used to deliver reaction reagents, including one or more of the following: biological samples, buffers, enzymes, primers, salts, and any other suitable agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides and/or various enzymes (e.g., polymerases, ligases, and proteases). Similarly, subsequent analysis of the cDNA library constructed from the RNAs present in the sample may be automated. For example, sequencing may be automated using a sequencing device and automated sequencing protocols as described above. In some embodiments, one or more of the devices or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, the steps of the methods described herein (e.g., those in Example 2) and/or aspects of the devices described herein may be automated using, for example, a computer system (e.g., a computer controlled system). A computer system on which aspects of the technology provided herein can be implemented may include a computer for any type of processing (e.g., sequence analysis and/or automated device control as described herein). In some embodiments, a computer system may include two or more computers. For example, one computer may be coupled, via a network, to a second computer. One computer may perform sequence analysis. The second computer may control one or more of the automated synthesis and assembly devices in the system. In other embodiments, additional computers may be included in the network to control one or more of the analysis or processing acts. Each computer may include a memory and processor. The computers can take any form, as the aspects of the methods provided herein are not limited to being implemented on any particular computer platform. Similarly, the network can take any form, including a private network or a public network. Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Sample Collection

Ordinary serum collection: A 10 mL whole blood sample was drawn into serum separator tubes. No anticoagulants were added. The whole blood sample was given 15-30 minutes to clot at room temperature with no disruptions. The sample was then centrifuged in refrigerated conditions for 10 minutes at 1000-2000 g. After centrifugation, the liquid supernatant, which contained serum, was transferred to clean polypropylene tubes using a Pasteur pipette. Multiple 1 mL aliquots were made and were stored at −80° C. The process was finished within the same day as the whole blood sample was collected to avoid potential degradation of proteins or nucleic acids in serum.

Fingertip serum collection: The collection site, usually on the tip of the left ring finger, was first cleaned with an alcohol wipe and then punctured with a lancet. At least 40 µL of blood was collected by gently touching the blood droplet formed at the puncture site with a plain capillary tube. Blood flew into the capillary tube due to capillary effect. The capillary tube was then sealed and left undisturbed for 30 minutes under room temperature to allow blood coagulation. The capillary tube with sample was then centrifuged under refrigerated conditions for 10 minutes at 1000 g and serum was harvested as supernatant after centrifugation. The harvested serum was made into aliquots and stored at −80° C.

Cell-free saliva collection: Firstly, a saliva collection swab was used to collect whole saliva from an individual. A swab was placed in the mouth under the tongue for at least 5 minutes, and then inserted into a syringe barrel for downstream processing. Secondly, cells were removed by either squeezing whole saliva out of the swab and pressing it through an attached 0.2 µm PES syringe filter or squeezing whole saliva out of the swab into a centrifuge tube and precipitating cells with refrigerated centrifugation at 1500 g for 15 minutes. The filtrate out of the syringe filter and supernatant after centrifugation were considered as cell-free saliva. The harvested cell-free saliva was made into aliquots and stored at −80° C.

IVF culture media sample collection: IVF cell culture media was usually provided cell-free and as aqueous droplets immersed in culture oil (e.g., OVOIL) in a petri dish. Firstly, the culture media droplets, having a typical volume of 30-50 µL, were transferred to centrifuge tubes with pipettes. Brief spin down was then applied to separate any oil phase carry over to the top and the aqueous phase at the bottom was aspirated out as IVF culture media into a new centrifuge tube. The harvested sample was made into aliquots and stored at −80° C.

Ordinary plasma collection: A 10 mL whole blood sample was drawn into anticoagulant-treated blood collection tubes using anticoagulants such as heparin, EDTA or citrate-acid. The sample was then centrifuged in refrigerated conditions for 10 minutes at 1000-2000 g. After centrifugation, the liquid supernatant, which was plasma, was transferred to clean polypropylene tubes using a Pasteur pipette. Multiple 1 mL aliquots were made and stored at −80° C.

Fingertip plasma collection: The collection site, usually on the tip of the left ring finger, was first cleaned with an alcohol wipe and then punctured with a lancet. At least 40 µL of blood was collected by gently touching the blood droplet formed at puncture site using a capillary tube coated with anticoagulant (e.g., heparin, EDTA, or citrate acid). Blood flew into the capillary tube due to capillary effect. The capillary tube was then sealed and centrifuged under refrigerated conditions for 10 minutes at 1000 g and plasma was harvested as supernatant after centrifugation. The harvested plasma was made into aliquots and stored at −80° C.

Example 2

Library Construction Procedures

Steps (a) to (o) below describe the construction of a cDNA library from the RNAs in the cell-free biological sample. The compositions and functions of the reagents and kits used in these steps are listed in Table 1.

TABLE 1

| Reagent or Kit | Composition or Commercial Catalog No. | Function |
| --- | --- | --- |
| Lysis Buffer | Nuclease-free water, 10 nM Tris HCl, 10% w/v SDS, 4% w/v NP-40 | Lyses, degrades, and dissociates membranes, exosomes, and ribonucleoproteins bound to the RNAs |
| Dithiothreitol (DTT) Solution | 11.5 mM DTT | Prevents oxidation |
| RNase Inhibitor | NEB #M0314 | Prevents RNA degradation by RNase |
| First Strand Primer Mix | A mixture of random primers (e.g., hexamers) and oligo-dT primers | Serves as primers for cDNA reverse transcription from RNAs |
| DNase Buffer | 3 mM MgCl$_2$ (reaction conc) 1 mM DTT (reaction conc) | Degrades any DNA present in the biological sample |

TABLE 1-continued

| Reagent or Kit | Composition or Commercial Catalog No. | Function |
| --- | --- | --- |
| HL-dsDNase | ArcticZymes #70800-201 | Degrades any DNA present in the biological sample |
| First Strand Buffer Mix | NEB #M0209 | Buffer for E. coli DNA polymerase I |
| First Strand Enzyme Mix | NEB #M0209 (E. coli DNA Polymerase I) | E. coli DNA Polymerase I used for first strand cDNA oligonucleotide synthesis with first strand primer mix |
| cDNA Processing Enzyme I (Fragmentase I) | NEB #M0348 | Enzyme to fragment DNA-RNA hybrid generated after first strand cDNA synthesis |
| cDNA Processing Enzyme II (Fragmentase II) | NEB #M0348 | Enzyme to fragment DNA-RNA hybrid generated after first strand cDNA synthesis |
| cDNA Processing Reagent I | Zinc ion ($Zn^{2+}$) | Buffer rich in heavy metal ion to facilitate RNA degradation |
| cDNA Processing Reagent II | EDTA | Buffer rich in EDTA to restore normal ionic strength |
| cDNA Processing Reagent III | NEB #M0201 | Buffer for T4 Polynucleotide Kinase |
| cDNA Processing Reagent IV | NEB #M0315 | Buffer for Terminal Transferase |
| cDNA Processing Enzyme III | NEB #M0201 (T4 Polynucleotide Kinase) | T4 Polynucleotide Kinase, repairs damaged 3' and 5' ends and ensures that there are phosphate groups on 5' ends and hydroxyl groups on 3' ends |
| cDNA Processing Enzyme IV | NEB #M0315 (Terminal Transferase) | Terminal Transferase, adds 3 guanines to 3' end of the first strand cDNA |
| Second Strand Buffer Mix | 50 mM Tris-HCl (pH 8.3), 75 mM KCl, 3 mM $MgCl_2$, 10 mM DTT | Buffer for MMLV Reverse Transcriptase |
| Second Primer Mix | | Second strand primer base pairing with the 3 guanines on first strand cDNA 3' end |
| Second Strand Enzyme Mix | Propspec #ENZ-310 (MMLV Reverse Transcriptase) | Reverse transcriptase used here for second strand cDNA synthesis, using first strand cDNA as template. |
| End Repair Enzyme Mix I | NEB #M0203 (T4 DNA Polymerase) | T4 DNA Polymerase, trims cDNA to blunt end |
| End Repair Enzyme Mix II | NEB #M0212 (Klenow exo-Fragment) | Klenow exo- Fragment to trim cDNA to blunt end and add adenine (A) to 3' end of the two strands of cDNA |
| Ligation Enzyme Mix | NEB #M0202 (T4 DNA Ligase) | T4 DNA Ligase, ligate adaptor to double-strand cDNA |
| Adaptor Inventory | | Barcoded adaptors for PCR amplification and multiplex sequencing |
| Ligation Buffer Mix | NEB #M0202 | Buffer for T4 DNA Ligase |
| Nuclease-free Water | Ambion #AM9916 | Nuclease-free water |
| AMPure beads | Beckman Coulter #A63987 | Nucleotide purification on beads |
| DNA Resuspension Buffer | 10 mM TRIS-Acetate, pH 8.0, reagent grade water; Or, TE Buffer (10 mM Tris-Acetate pH 8.0, 1 mM EDTA) | Buffer used for DNA storage media or elution media (from magnetic beads) |
| Amplification Buffer Mix | NEB #E5000 | Buffer for Taq DNA Polymerase, also contains dNTP |
| Amplification Primer Mix I | | Primers base-pairing with adaptor for amplification, with the "reverse primer" consists of dUTP instead of thymine |
| Amplification Enzyme Mix | NEB #E5000 (Taq DNA Polymerase) | Taq DNA Polymerase, used for PCR amplification |
| rRNA Depletion Primer Mix | | Primer that base-pairs with specific human rRNA region |
| Strand Selection Enzyme Mix | NEB #M0280 (uracil DNA glycosylase) | Uracil DNA glycosylase (UDG), degrades the specific cDNA strand containing dUTP or a uracil DNA glycosylase recognition sequence |

TABLE 1-continued

| Reagent or Kit | Composition or Commercial Catalog No. | Function |
| --- | --- | --- |
| Adaptor Cleavage Enzyme Mix | Restriction Endonuclease | Restriction endonuclease to cleave adaptor off during rRNA depletion so that cDNA strands carrying rRNA information is not amplifiable |
| Amplification Primer Mix II | | Primers base-pairing with adaptor for amplification |
| Double-strand DNA quantification kit A | Thermo Fisher #32851 | Quantification tool for cDNA concentration in constructed library |
| Double-strand DNA gel electrophoresis array kit B | Aligent #5067-4626 | Examine cDNA size distribution in constructed library | a. Exosome Lysis and Nucleoprotein Dissociation

1. Thaw unprocessed serum samples from Example 1 on ice. Load 7 µL of the unprocessed serum sample to each well of a PCR strip or PCR plate.
2. Take "Lysis Buffer" out of stock, vortex to mix, spin down, and keep at room temperature. Take "DTT Solution" out from −20° C. storage, thaw at room temperature, vortex to mixt, spin down, and keep at room temperature. Take "RNase Inhibitor" out from −20° C. storage, flick gently to mix, spin down, and put on ice.
3. Prepare the lysis cocktail by mixing the following components (the volume for each component is for one lysis reaction): Lysis Buffer: 2.8 µL, DTT Solution: 1.7 µL, and RNase Inhibitor: 0.5 µL. Mix the components thoroughly by pipetting up and down at least 10 times with 70% of total volume. Then spin down and put the lysis cocktail on ice. Use immediately.
4. Add 5 µL of the lysis cocktail from step (a)(3) to the 7 µL unprocessed serum sample from step (a)(1) for a final volume of 12 µL. Mix thoroughly by pipetting up and down for at least 10 times. Incubate at room temperature for 5 minutes. Proceed immediately to the next step of primer annealing and DNA digestion or store the mixture at −80° C.

b. Primer Annealing and DNA Digestion

1. Pre-warm thermal cycler to run Program 1 (70° C. for 2 min, hold at 4° C.). Take "DNase Buffer" and "First Strand Primer Mix (mixture of random and oligo-dT primer)" out from −20° C. storage, thaw under room temperature, vortex to mix, spin down, and keep on ice.
2. Prepare the primer annealing cocktail by mixing the following components (the volume for each component is for one annealing reaction): DNase Buffer: 1 µL and First Strand Primer Mix: 2.6 µL. Mix thoroughly by pipetting up and down at least 10 times with 70% of total volume. Then spin down and put on ice. Use immediately.
3. Add 3.6 µL of the primer annealing cocktail from step (b)(2) to each sample tube in step (a)(4) for a total volume of 15.6 µL. Mix thoroughly by pipetting up and down for at least 10 times. Spin down and place on ice.
4. Place the tube from step (b)(3) in the pre-warmed thermal cycler and start Program 1 (70° C. for 2 min, hold at 4° C.). Remove the tube from the thermal cycler, spin down the condensation, and place the tube on ice. Proceed to the next step.
5. Pre-warm thermal cycler to run Program 2 (37° C. for 10 min, 65° C. for 5 min, hold at 4° C.). Take "HL-dsDNase" and "RNase Inhibitor" out from −20° C. storage, flick gently to mix, spin down, and keep on ice.
6. Prepare a DNA digestion cocktail by mixing the following components (the volume for each component is for one digestion reaction): HL-dsDNase: 2 µL and RNase Inhibitor: 0.2 µL. Mix thoroughly by pipetting up and down at least 10 times with 70% of total volume. Then spin down and put on ice. Use immediately.
7. Add 2.2 µL of the DNA digestion cocktail from step (b)(6) to each sample tube from step (b)(4) for a total volume of 17.8 µL. Mix thoroughly by pipetting up and down for at least 10 times. Spin down and place on ice.
8. Place the tube in the pre-warmed thermal cycler and start Program 2 (37° C. for 10 min, 65° C. for 5 min, hold at 4° C.). Remove the tube out of the thermal cycler, spin down the condensation, and place on ice, proceed to the next step of first strand cDNA synthesis.

c. First Strand cDNA Synthesis

1. Pre-warm thermal cycler to run Program 3 (25° C. for 5 min, 40° C. for 30 min, 70° C. for 10 min, hold at 4° C.). Take "First Strand Buffer Mix (buffer for *E. coli* DNA polymerase I)" out from −20° C. storage, thaw under room temperature, vortex to mix, spin down, and keep on ice. Take "First Strand Enzyme Mix (*E. coli* DNA Polymerase I)" and "RNase Inhibitor" out from −20° C. storage, flick gently to mix, spin down, and keep on ice.
2. Prepare a first strand synthesis cocktail by mixing the following components (the volume for each component is for one synthesis reaction): First Strand Buffer Mix: 1 µL, First Strand Enzyme Mix: 1 µL and RNase Inhibitor 0.2 µL. Mix thoroughly by pipetting up and down at least 10 times with 70% of total volume. Then spin down and put on ice. Use immediately.
3. Add 2.2 µL of the first strand synthesis cocktail from step (c)(2) to each sample tube from step (b)(8) for a total volume of 20 µL. Mix thoroughly by pipetting up and down for at least 10 times. Spin down and place on ice.

d. cDNA Processing

1. Pre-warm thermal cycler to run Program 4 (37° C. for 30 min, hold at 4° C.). Take "cDNA Processing Enzyme I (Fragmentase I)" and "cDNA Processing Enzyme II (Fragmentase II)" out from −20° C. storage, flick gently to mix, spin down, and keep on ice. Take "cDNA Processing Reagent I (buffer rich in heavy metal ion to facilitate RNA degradation)", "cDNA Processing Reagent II (buffer rich in EDTA to restore normal ionic strength)", "cDNA Processing Reagent III (buffer for T4 Polynucleotide Kinase)" and "cDNA Processing Reagent IV (buffer for Terminal Transferase)" out from −20° C. storage, thaw under room temperature, vortex to mix, spin down, and keep on ice.

2. Prepare cDNA fragmenting cocktail by mixing the following components (the volume for each component is for one fragmenting reaction): cDNA Processing Enzyme I: 0.5 μL and cDNA Processing Enzyme II: 0.5 μL. Mix thoroughly by pipetting up and down at least 10 times with 70% of total volume. Then spin down and put on ice. Use immediately.
3. Add 1 μL of the cDNA processing cocktail to each sample tube from step (c)(3) for a total volume of 21 μL. Mix thoroughly by pipetting up and down for at least 10 times. Spin down and place on ice.
4. Place the tube in the pre-warmed thermal cycler and start Program 4 (37° C. for 30 min, hold at 4° C.). Remove the tube out of the thermal cycler, spin down the condensation, and place on ice. Proceed to the next step immediately.
5. Pre-warm thermal cycler to run Program 5 (90° C. for 20 min, hold at 4° C.).
6. Add 2 μL of "cDNA Processing Reagent I (buffer rich in heavy metal ion to facilitate RNA degradation)" to each sample tube from step (d)(4) for a total volume of 23 μL. Mix thoroughly by pipetting up and down for at least 10 times. Spin down and place on ice.
7. Place the tube in the pre-warmed thermal cycler and start Program 5 (90° C. for 20 min, hold at 4° C.). Remove the tube out of the thermal cycler, spin down the condensation, and place on ice. Proceed to the next step immediately.
8. Add 2 μL of "cDNA Processing Reagent II (buffer rich in EDTA to restore normal ionic strength)" to each sample tube from step (d)(7) for a total volume of 25 μL. Mix thoroughly by pipetting up and down for at least 10 times. Spin down and place on ice.
9. Pre-warm thermal cycler to run Program 6 (37° C. for 30 min, 70° C. for 10 min, hold at 4° C.). Take "cDNA Processing Enzyme III (T4 Polynucleotide Kinase to repair damaged 3' and 5' ends)" out from −20° C. storage, flick gently to mix, spin down, and keep on ice.
10. Prepare a cDNA repair cocktail by mixing the following components (the volume for each component is for one repair reaction): cDNA Processing Reagent III: 1 μL and cDNA Processing Enzyme III: 1 μL. Mix thoroughly by pipetting up and down at least 10 times with 70% of total volume. Then spin down and put on ice. Use immediately.
11. Add 2 μL of the cDNA repair cocktail to each sample tube from step (d)(8) for a total volume of 27 μL. Mix thoroughly by pipetting up and down for at least 10 times. Spin down and place on ice.
12. Place the tube in the pre-warmed thermal cycler and start Program 6 (37° C. for 30 min, 70° C. for 10 min, hold at 4° C.). Remove the tube out of the thermal cycler, spin down the condensation, and place on ice. Proceed to the next step immediately.
13. Pre-warm thermal cycler to run Program 7 (37° C. for 30 min, 75° C. for 20 min, hold at 4° C.). Take "cDNA Processing Enzyme IV (Terminal Transferase to add 3 guanine to 3' end of the first strand cDNA)" out from −20° C. storage, flick gently to mix, spin down, and keep on ice.
14. Prepare a cDNA transferase cocktail by mixing the following components (the volume for each component is for one transferase reaction): cDNA Processing Reagent IV: 7 μL and cDNA Processing Enzyme IV: 1 μL. Mix thoroughly by pipetting up and down at least 10 times with 70% of total volume. Then spin down and put on ice. Use immediately.
15. Add 8 μL of the cDNA transferase cocktail to each sample tube from step (d)(12) for a total volume of 35 μL. Mix thoroughly by pipetting up and down for at least 10 times. Spin down and place on ice.
16. Place the tube in the pre-warmed thermal cycler and start Program 7 (37° C. for 30 min, 75° C. for 20 min, hold at 4° C.). Remove the tube out of the thermal cycler, spin down the condensation, and place on ice. Proceed to the next step of second strand cDNA synthesis immediately.

e. Second Strand Synthesis

1. Pre-warm thermal cycler to run Program 8 (25° C. for 15 min, 37° C. for 15 min, 70° C. for 10 min, hold at 4° C.). Take "Second Strand Buffer Mix (buffer for MMLV Reverse Transcriptase)" and "Second Primer Mix (second strand primer base paring with the 3 guanines on first strand cDNA 3' end)" out from −20° C. storage, thaw at room temperature, vortex to mix, spin down, and keep on ice. Take "Second Strand Enzyme Mix (MMLV Reverse Transcriptase)" out from −20° C. storage, flick gently to mix, spin down, and keep on ice.
2. Prepare a second strand synthesis cocktail by mixing the following components (the volume for each component is for one synthesis reaction): Second Strand Buffer Mix: 3.5 μL, Second Strand Primer Mix: 3.5 μL, and Second Strand Enzyme Mix: 1 μL. Mix thoroughly by pipetting up and down at least 10 times with 70% of total volume. Then spin down and put on ice. Use immediately.
3. Add 8 μL of the second strand synthesis reaction to each sample tube from step (d)(15) for a volume of 43 μL. Mix thoroughly by pipetting up and down for at least 10 times. Spin down and place on ice.
4. Place the tube in the pre-warmed thermal cycler and start Program 8 (25° C. for 15 min, 37° C. for 15 min, 70° C. for 10 min, hold at 4° C.). Remove the tube out of the thermal cycler, spin down the condensation, and place on ice. Proceed to the next step immediately.

f. End Repair

1. Pre-warm thermal cycler to run Program 9 (25° C. for 30 min, 70° C. for 10 min, hold at 4° C.). Take "End Repair Enzyme Mix I (T4 DNA Polymerase to trim cDNA to blunt end)" and "End Repair Enzyme Mix II (Klenow exo-Fragment to trim cDNA to blunt end and add adenine to 3' end of the two strands of cDNA)" out from −20° C. storage, flick gently to mix, spin down, and keep on ice.
2. Prepare an end repair cocktail by mixing the following components (the volume for each component is for one repair reaction): End Repair Enzyme Mix I: 1 μL and End Repair Enzyme Mix II: 1 μL. Mix thoroughly by pipetting up and down at least 10 times with 70% of total volume. Then spin down and put on ice. Use immediately.
3. Add 2 μL of the end repair cocktail to each sample tube from step (e)(4) for a total volume of 45 μL. Mix thoroughly by pipetting up and down for at least 10 times. Spin down and place on ice.
4. Place the tube in the pre-warmed thermal cycler and start Program 9 (25° C. for 30 min, 70° C. for 10 min, hold at 4° C.). Remove the tube out of the thermal cycler, spin down the condensation, and place on ice. Proceed to the next step of "Adaptor Ligation" immediately or store the mixture at −20° C.

g. Adaptor Ligation

1. Pre-warm thermal cycler to run Program 10 (25° C. for 30 min, 70° C. for 10 min, hold at 4° C.). Take "Ligation Enzyme Mix (T4 DNA Ligase)" out from −20° C. storage, flick gently to mix, spin down, and keep on ice. Take "Adaptor Inventory (barcoded adaptors for PCR amplification and multiplex sequencing)" out from −20° C. storage, thaw under room temperature, vortex to mix, spin down, and keep on ice. Take "Ligation Buffer Mix (buffer for T4 DNA Ligase)" and "Nuclease-free Water" out from −20° C. storage, thaw under room temperature, vortex to mix, spin down, and keep on ice. Take "AMPure beads (Magnetic beads for nucleotide purification)" out from 4° C. storage and "DNA Resuspension Buffer (10 mM TRIS-Acetate, pH 8.0, reagent grade water or, TE Buffer [10 mM Tris-Acetate pH 8.0, 1 mM EDTA])" out from −20° C. storage, equilibrate, and thaw at room temperature for at least 30 minutes before the next step of "Adaptor Ligation Purification."

2. Add 3.25 μL of different appropriate barcoded adaptors to each of the tubes from step (0(4) for a total volume of 48.25 μL. Mix thoroughly by pipetting. Then spin down and place on ice.

3. Prepare a ligation cocktail by mixing the following components (the volume for each component is for one ligation reaction): Ligation Buffer Mix: 13 μL, Ligation Enzyme Mix: 2 μL, and Nuclease-free Water: 1.75 μL. Mix thoroughly by pipetting up and down at least 10 times with 70% of total volume. Then spin down and put on ice. Use immediately.

4. Add 16.75 μL of the ligation cocktail to each sample tube from step (g)(2) for a total volume of 65 μL. Mix thoroughly by pipetting up and down for at least 10 times. Spin down and place on ice.

5. Place the tube in the pre-warmed thermal cycler and start Program 10 (25° C. for 30 min, 70° C. for 10 min, hold at 4° C.). Remove the tube out of the thermal cycler, spin down the condensation, and place on ice. Proceed to the next step of "Adaptor Ligation Purification" immediately or store the mixture at −20° C.

h. Adaptor Ligation Purification (Conducted at Room Temperature)

1. Make sure that "AMPure beads" and "DNA Resuspension Buffer" are thawed completely and are equilibrated to room temperature. This usually takes at least 30 minutes. Vortex "AMPure beads" and "DNA Resuspension Buffer" to resuspend and mix. Leave the reagents at room temperature. Do not spin down beads. Take "Nuclease-free Water" out from −20° C. storage, thaw under room temperature, vortex to mix, spin down, and keep at room temperature. Make sure "AMPure Beads" are fully suspended before use. Prepare 70% ethanol freshly.

2. Add 35 μL "Nuclease-free Water" to each tube from step (g)(5) for a volume of 100 μL. Then add 100 μL beads suspension to each tube (beads volume/sample volume=1). Mix the 200 μL mixture by pipetting up and down. Leave at room temperature.

3. Incubate at room temperature for 10 minutes.

4. Transfer the tubes to a magnet and let stand for at least 10 minutes for a complete separation of beads. Wait longer if necessary. Then discard all 200 μL liquid phase. Make sure that beads are not dispersing to avoid beads loss. Do not remove tubes from the magnet yet.

5. Add 200 μL freshly prepared 70% ethanol with the tubes still on magnet, let stand for 30 sec, then discard the all liquid phase using a pipette. Repeat one more time for a total of two ethanol washes. For the second wash, remove as much liquid phase as possible; the leftover liquid may affect results. Do not remove tubes from the magnet yet.

6. Air dry the beads in the tubes for around 10 minutes on magnet. Make sure beads are completely dried and avoid over dry. It is important to have all residual ethanol removed. Time needed to dry may varies depend on the experimental environment. Check every 2 minutes to avoid over dry. Remove tubes from the magnet.

7. Add 30 μL the "DNA Resuspension Buffer" that is already equilibrate to room temperature to the dried beads. Flick the tubes to suspend the beads, vortex, and pulse spin down if necessary.

8. Transfer the tubes to a magnet and let stand for at least 5 minutes for a complete separation of beads. Wait longer if necessary. Then transfer all 30 μL liquid phase to a set of new tubes (or plates). Proceed to the next step of "First Stage Library Amplification" immediately or store the mixture at −20° C.

i. First Stage Library Amplification (18 Rounds)

1. Pre-warm thermal cycler to run Program 12 (70° C. for 10 min, 18 cycles of: 94° C. for 30 sec+60° C. for 30 sec+72° C. for 1 min, 72° C. for 5 min, hold at 10° C.). Take "Amplification Buffer Mix (buffer for Taq DNA Polymerase)" and "Amplification Primer Mix I (primers base-pairing with adaptor for amplification, with the 'reverse primer' consist of dUTP instead of thymine)" out from −20° C. storage, thaw under room temperature, vortex to mix, spin down, and keep at room temperature. Take "Amplification Enzyme Mix (Taq DNA Polymerase)" out from −20° C. storage, flick gently to mix, spin down, and keep on ice. Take "AMPure beads" out from 4° C. storage and "DNA Resuspension Buffer" out from −20° C. storage, equilibrate and thaw at room temperature for at least 30 minutes before the next step of "First Round Library Purification."

2. Prepare a first stage amplification cocktail by mixing the following components (the volume for each component is for one amplification reaction): Amplification Buffer Mix: 10 μL, Amplification Primer Mix I: 9.5 μL, and Amplification Enzyme Mix: 0.5 μL. Mix thoroughly by pipetting up and down at least 10 times with 70% of total volume. Then spin down and put on ice. Use immediately.

3. Add 20 μL of the first stage amplification cocktail to each sample tube from step (g)(8) for a total volume of 50 μL. Mix thoroughly by pipetting up and down for at least 10 times. Spin down and place on ice.

4. Place the tube in the pre-warmed thermal cycler and start Program 12 (70° C. for 10 min, 18 cycles of: 94° C. for 30 sec+60° C. for 30 sec+72° C. for 1 min, 72° C. for 5 min, hold at 10° C.). Remove the tube out of the thermal cycler, spin down the condensation and place on ice. Proceed to the next step of "First Round Library Purification" immediately or store the mixture at −20° C.

j. First Round Library Purification (Conducted at Room Temperature)

1. Make sure that "AMPure Beads" and "DNA Resuspension Buffer" are thawed completely and are equilibrated to room temperature. This usually takes at least 30 minutes. Vortex "AMPure Beads" and "DNA Resuspension Buffer" to resuspend and mix. Leave the reagents at room temperature. Do not spin down beads. Make sure "AMPure Beads" are fully suspended before use. Prepare 70% ethanol freshly.

2. Add 40 μL beads suspension to each tube from step (i)(4) for a total volume of 90 μL (beads volume/sample volume=0.8). Mix the 90 μL mixture by pipetting up and down. Leave at room temperature.

3. Incubate at room temperature for 10 minutes.

4. Transfer the tubes to a magnet and let stand for at least 5 minutes for a complete separation of beads. Wait longer if necessary. Then discard all 90 μL liquid phase. Make sure that beads are not dispersing to avoid beads loss. Do not remove tubes from the magnet yet.

5. Add 200 μL freshly prepared 70% ethanol with the tubes still on magnet, let stand for 30 sec, then discard the all liquid phase using pipettes. Repeat one more time for a total of two washes. For the second wash, remove as much liquid phase as possible; the leftover liquid may affect results. Do not remove tubes from the magnet yet.
6. Air dry the beads in the tubes for around 10 minutes on magnet. Make sure beads are completely dried, but avoid over drying. It is important to have all residual ethanol removed. Time needed to dry may varies depend on the experimental environment. Check every 2 minutes to avoid over drying. Remove tubes from the magnet.
7. Add 50 µL "DNA Resuspension Buffer" that is already equilibrate to room temperature to dried beads. Flick the tubes to suspend the beads, vortex, and pulse spin down if necessary.
8. Transfer the tubes to a magnet and let stand for at least 5 minutes for a complete separation of beads. Wait longer if necessary. Then transfer all 50 µL liquid phase to a set of new tubes (or plates). Leave at room temperature.
9. At room temperature, add 40 µL beads suspension to each tube from step (j)(8) for a total volume of 90 µL (beads volume/sample volume=0.8). Mix the 90 µL mixture by pipetting up and down. Leave at room temperature.
10. Incubate at room temperature for 10 minutes.
11. Transfer the tubes to a magnet and let stand for at least 5 minutes for a complete separation of beads. Wait longer if necessary. Then discard all 90 µL liquid phase. Make sure that beads are not dispersing to avoid beads loss. Do not remove tubes from the magnet yet.
12. Add 200 µL freshly prepared 70% ethanol with the tubes still on magnet, let stand for 30 sec, then discard all liquid phase using pipettes. Repeat one more time for a total of two ethanol washes. For the second wash, remove as much liquid phase as possible; the leftover liquid may affect results. Do not remove tubes from the magnet yet.
13. Air dry the beads in the tubes for around 10 minutes on magnet. Make sure beads are completely dried and avoid over drying. It is important to have all residual ethanol removed. Time needed to dry may varies depend on the experimental environment. Check every 2 minutes to avoid over drying. Remove tubes from the magnet.
14. Add 25 µL "DNA Resuspension Buffer" that is already equilibrate to room temperature to dried beads. Flick the tubes to suspend the beads, vortex, and pulse spin down if necessary.
15. Transfer the tubes to a magnet and let stand for at least 5 minutes for a complete separation of beads. Wait longer if necessary. Then transfer all 25 µL liquid phase to a set of new tubes (or plates). Proceed to the next step of "Check Point I—cDNA Quantification" immediately or store the mixture at −20° C.

k. Check Point I—cDNA Quantification
1. Quantify cDNA in library with double-strand DNA quantification kit A. Leave at least 8.5 µL of sample for the next step of "rRNA Depletion." cDNA concentration in the sample should be greater than 10 pg/µL.

1. rRNA Depletion and Strand Selection
1. Pre-warm thermal cycler to run Program 13 (37° C.—10 min, 95° C.—2 min, 50° C.—1 min, 65° C.—10 min, hold at 4° C.). Take "Amplification Buffer Mix", "rRNA Depletion Primer Mix (primer that base-pair with specific human rRNA region)" and "Nuclease-free Water" out from −20° C. storage, thaw at room temperature, vortex to mix, spin down, and keep on ice. Take "Strand Selection Enzyme Mix (uracil DNA glycosylase to degrade the specific cDNA strand containing dUTP)", "Amplification Enzyme Mix (Taq DNA Polymerases)" and "Adaptor Cleavage Enzyme Mix (Restriction Endonuclease)" out from −20° C. storage, flick gently to mix, spin down, and keep on ice.
2. Load a set of new PCR tubes/plates with 10 ng or at most 8.5 µL of cDNA library. Add "Nuclease-free Water" to make a total volume of 8.5 µL if necessary.
3. Prepare a strand selection cocktail by mixing the following components (the volume for each component is for one strand selection reaction): Amplification Buffer Mix: 5 µL, rRNA Depletion Primer Mix: 10 µL, Strand Selection Enzyme Mix: 0.5 µL, and Amplification Enzyme Mix: 1 µL. Mix thoroughly by pipetting up and down at least 10 times with 70% of total volume. Then spin down and put on ice. Use immediately.
4. Add 16.5 µL of the strand selection cocktail to each sample tube for a total volume of 25 µL. Mix thoroughly by pipetting up and down for at least 10 times. Spin down and place on ice.
5. Place the tube in the pre-warmed thermal cycler and start Program 13 (37° C. for 10 min, 95° C. for 2 min, 50° C. for 1 min, 65° C. for 10 min, hold at 4° C.). Remove the tube out of the thermal cycler, spin down the condensation, and place on ice.
6. Pre-warm thermal cycler to run Program 14 (55° C. for 30 min, 95° C. for 5 min, hold at 4° C.).
7. Prepare an adaptor cleavage cocktail by mixing the following components (the volume for each component is for one adaptor cleavage reaction): Amplification Buffer Mix: 5 µL, Adaptor Cleavage Enzyme Mix: 2.5 µL, and Nuclease-free Water: 17.5 µL. Mix thoroughly by pipetting up and down at least 10 times with 70% of total volume. Then spin down and put on ice. Use immediately.
8. Add 25 µL of the adaptor cleavage cocktail to each sample tube from step (1)(5) for a total volume of 50 µL. Mix thoroughly by pipetting up and down for at least 10 times. Spin down and place on ice.
9. Place the tube in the pre-warmed thermal cycler and start Program 14 (55° C. for 30 min, 95° C. for 5 min, hold at 4° C.). Remove the tube out of the thermal cycler, spin down the condensation, and place on ice. Proceed to the next step of "Second Stage Library Amplification" immediately or store the mixture at −20° C.

m. Second Stage Library Amplification (8 Rounds)
1. Pre-warm thermal cycler to run Program 15 (95° C. for 2 min, 2 cycles of: 95° C. for 30 sec+60° C. for 90 sec, 6 cycles of: 95° C. for 30 sec+65° C. for 90 sec, 65° C. for 5 min, hold at 4° C.). Take "Amplification Buffer Mix" and "Amplification Primer Mix II (primers base-pairing with adaptor for amplification)" out from −20° C. storage, thaw under room temperature, vortex to mix, spin down, and keep at room temperature. Take "Amplification Enzyme Mix" out from −20° C. storage, flick gently to mix, spin down and keep on ice. Take "AMPure beads" out from 4° C. storage and "DNA Resuspension Buffer" out from −20° C. storage, equilibrate and thaw at room temperature for at least 30 minutes before the step of "Second Round Library Purification."
2. Prepare a second stage amplification cocktail by mixing the following components (the volume for each component is for one amplification reaction): Amplification Buffer Mix: 10 µL, Amplification Primer Mix II: 39.5 µL, and Amplification Enzyme Mix: 0.5 µL. Mix thoroughly by pipetting up and down at least 10 times with 70% of total volume. Then spin down and put on ice. Use immediately.
3. Add 50 µL of the second stage amplification cocktail to each sample tube from step (1)(9) for a total volume of 100 µL. Mix thoroughly by pipetting up and down for at least 10 times. Spin down and place on ice.

4. Place the tube in the pre-warmed thermal cycler and start Program 15 (95° C. for 2 min, 2 cycles of: 95° C. for 30 sec+60° C. for 90 sec, 6 cycles of: 95° C. for 30 sec+65° C. for 90 sec, 65° C. for 5 min, hold at 4° C.). Remove the tube out of the thermal cycler, spin down the condensation, and place on ice. Proceed to the next step of "Second Round Library Purification" immediately or store the mixture at −20° C.

n. Second Round Library Purification (Conducted at Room Temperature)

1. Make sure that "AMPure Beads" and "DNA Resuspension Buffer" are thawed completely and are equilibrated to room temperature. This usually takes at least 30 minutes. Vortex "AMPure Beads" and "DNA Resuspension Buffer" to resuspend and mix. Leave the reagents at room temperature. Do not spin down beads. Make sure "AMPure Beads" are fully suspended before use. Prepare 70% ethanol freshly.
2. Add 100 µL beads suspension to each tube from step (m)(4) for a total volume of 200 µL (beads volume/sample volume=1). Mix the 200 µL mixture by pipetting up and down. Leave at room temperature.
3. Incubate at room temperature for 10 minutes.
4. Transfer the tubes to a magnet and let stand for at least 10 minutes for a complete separation of beads. Wait longer if necessary. Then discard all 200 µL liquid phase. Make sure that beads are not dispersing to avoid beads loss. Do not remove tubes from the magnet yet.
5. Add 200 µL freshly prepared 70% ethanol with the tubes still on magnet, stand for 30 sec, then discard the all liquid phase using pipettes. Repeat one more time for a total of two ethanol washes. For the second wash, remove as much liquid phase as possible; the leftover liquid may affect results. Do not remove tubes from the magnet yet.
6. Air dry the beads in the tubes for around 10 minutes on magnet. Make sure beads are completely dried and avoid over drying. It is important to have all residual ethanol removed. Time needed to dry may varies depend on the experimental environment. Check every 2 minutes to avoid over drying. Remove tubes from the magnet.
7. Add 50 µL "DNA Resuspension Buffer" that is already equilibrate to room temperature to dried beads. Flick the tubes to suspend the beads, vortex, and pulse spin down if necessary.
8. Transfer the tubes to a magnet and let stand for at least 5 minutes for a complete separation of beads. Wait longer if necessary. Then transfer all 50 µL liquid phase to a set of new tubes (or plates). Leave at room temperature.
9. At room temperature, add 50 µL beads suspension to each tube from step (n)(8) for a volume of 90 µL (beads volume/sample volume=1). Mix the 100 µL mixture by pipetting up and down. Leave at room temperature.
10. Incubate at room temperature for 10 minutes.
11. Transfer the tubes to a magnet and let stand for at least 5 minutes for a complete separation of beads. Wait longer if necessary. Then discard all 100 µL liquid phase. Make sure that beads are not dispersing to avoid beads loss. Do not remove tubes from the magnet yet.
12. Add 200 µL freshly prepared 70% ethanol with the tubes still on magnet, stand for 30 sec, then discard all liquid phase using pipettes. Repeat one more time for a total of two ethanol washes. For the second wash, remove as much liquid phase as possible; the leftover liquid may affect results. Do not remove tubes from the magnet yet.
13. Air dry the beads in the tubes for around 10 minutes on magnet. Make sure beads are completely dried to avoid over drying. It is important to have all residual ethanol removed. Time needed to dry may varies depend on the experimental environment. Check every 2 minutes to avoid over drying. Remove tubes from the magnet.
14. Add 25 µL "DNA Resuspension Buffer" that is already equilibrate to room temperature to dried beads. Flick the tubes to suspend the beads, vortex, and pulse spin down if necessary.
15. Transfer the tubes to a magnet and let stand for at least 5 minutes for a complete separation of beads. Wait longer if necessary. Then transfer all 25 µL liquid phase to a set of new tubes (or plates). Proceed to the next step of "Check Point II—cDNA Quantity and Quality" immediately or store the mixture at −20° C.

o. Check Point II—cDNA Quantity and Quality

1. Quantify cDNA in library with double-strand DNA quantification kit A. cDNA Concentration should be greater than 1 nM.
2. Check the quality of cDNA in library with double-strand DNA gel electrophoresis array kit B. Most of the cDNA molecules should have sizes round 300 base pair. The range of cDNA molecules should be around 200 to 600 base-pair.

Example 3

Observed Gene Complexity and Tissue Specific Genes

Overall Diversity of Detected Genes in Serum

We used three serums from three different individuals, indicated by serum A, B, and C, to investigate the number of different categories of genes that can be detected with the present method. By applying the present method, after sequencing and mapping genes having ENSEMBL gene annotation HG38, a large diversity of genes was observed with high consistency over all three serums, with the "effective" serum input volume being 45 µL, 61 µL, and 61 µL, respectively, for serum A, B, and C. The yields of the sequencing reads were 40.4 million, 64.9 million, and 50.2 million, respectively. The number of genes detected from serum A, B, and C were 50606, 50949, and 50544, respectively, each of which fell in the same 42 out of 44 human gene categories. These categories included, most importantly, protein-coding genes, lincRNA, miRNA, and snRNA, etc., which were crucial for basic functions and regulations. With sequencing data from all libraries from each serum combined, the percentages of genes detected in different categories annotated with ENSEMBL gene annotation HG38 were as follows: in serum A: 95% of all protein coding genes, 92% of all lincRNA, 41% of all miRNA, and 67% of all snRNA were detected; in serum B: 95% of all protein coding genes, 93% of all lincRNA, 42% of all miRNA, and 65% of all snRNA were detected; in serum C: 94% of all protein coding genes, 93% of all lincRNA, 41% of all miRNA, and 63% of all snRNA were detected. Table 2 below lists the specific numbers of genes detected in each of the following gene categories: protein-coding gene, lincRNA, miRNA, and snRNA (ENSEMBL gene annotation HG38 was used as reference genome). The total number of genes for each category is shown in the parenthesis after the name of each gene category.

TABLE 2

| Serum | Protein-coding Gene (19826) | | lincRNA (7668) | | miRNA (4198) | | snRNA (1905) | |
|---|---|---|---|---|---|---|---|---|
| | Number | Percent | Number | Percent | Number | Percent | Number | Percent |
| A | 18769 | 95% | 7073 | 92% | 1708 | 41% | 1268 | 67% |
| B | 18784 | 95% | 7116 | 93% | 1781 | 42% | 1236 | 65% |
| C | 18716 | 94% | 7096 | 93% | 1718 | 41% | 1197 | 63% |

In summary, large and consistent gene diversity was observed among all three serums with the present method. Genes were detected in the same 42 out of all 44 human gene categories with all three serums covering both recurrence and non-recurrence status. Important categories such as protein coding genes, lincRNA, miRNA, and snRNA were studied as examples. Almost all protein coding genes (>94%), most of lincRNA (>92%), and around 41% and 65% of all miRNA and snRNA, respectively, could be detected using about 45 μL of serum A and about 61 μL of each of serum B and serum C. High consistency of gene diversity was observed among three serums, even though they were from different individuals.

Overall Diversity of Detected Genes in Cell-Free Saliva

Cell-free saliva D from an individual was analyzed to investigate the diversity of genes that could be detected. With the current method applied, after sequencing and mapping harvested data to ENSEMBL gene annotation HG38, a large diversity of genes was observed. From the "effective" volume of 13 μL cell-free saliva input, around 6.4 million sequencing reads were generated and a total of 24897 genes was detected. These genes belong to various of categories, and most importantly, protein-coding genes, lincRNA, miRNA, snRNA, etc. 14215 out of all 19826 protein-coding genes, 3040 out of all 7668 lincRNA, 211 out of all 4198 miRNA, and 179 out of all 1905 snRNA were identified. Table 3 below lists the specific numbers of genes detected in each of the following gene categories: protein-coding gene, lincRNA, miRNA, and snRNA (ENSEMBL gene annotation HG38 was used as reference genome), and the corresponding percentage. The total number of genes for each category is shown in the parenthesis after the name of each gene category.

TABLE 3

| Cell-free Saliva | Protein-coding Gene (19826) | | lincRNA (7668) | | miRNA (4198) | | snRNA (1905) | |
|---|---|---|---|---|---|---|---|---|
| | Number | Percent | Number | Percent | Number | Percent | Number | Percent |
| D | 14215 | 72% | 3040 | 40% | 211 | 5% | 179 | 9% |

In summary, a large diversity of genes was detected from cell-free saliva with the present method. There were 24897 different genes detected from 13 μL cell-free saliva and the genes were also diverse in terms of categories. Using the four important gene categories as examples, the majority (72%) of protein-coding genes, a large proportion (40%) of lincRNA as well as some miRNA, and snRNA were identified.

Overall Diversity of Detected Genes in IVF Culture Media

The diversity of genes that could be detected in IVF culture media was studied using exemplary IVF culture media E. With the method above, after sequencing and mapping harvested data to ENSEMBL gene annotation HG38, numerous genes from a diverse of gene categories were observed. Around 5.2 million sequencing reads were generated and as many as 31346 genes from various gene categories were detected in 7 μL IVF culture media input, with the most important gene categories being protein-coding genes, lincRNA, miRNA, snRNA, etc. Among all protein-coding genes, 15163 could be identified; the numbers were 4431 for lincRNA, 420 for miRNA, and 483 for snRNA. Table 4 below lists the specific numbers of genes detected in each of the following gene categories: protein-coding gene, lincRNA, miRNA, and snRNA (ENSEMBL gene annotation HG38 was used as reference genome), and the corresponding percentage. The total number of genes for each category is shown in the parenthesis after the name of each gene category.

TABLE 4

| IVF Media | Protein-coding Gene (19826) | | lincRNA (7668) | | miRNA (4198) | | snRNA (1905) | |
|---|---|---|---|---|---|---|---|---|
| | Number | Percent | Number | Percent | Number | Percent | Number | Percent |
| E | 15163 | 76% | 4431 | 58% | 420 | 10% | 483 | 25% |

In summary, a large number of genes from a variety of categories was identified in IVF culture media with the present method. A total of 31346 genes were detected in 7 μL IVF culture media and these genes were from diverse gene categories. For example, among the most important gene categories, the majority (76%) of protein-coding genes, a large proportion (58%) of lincRNA, as well as a proportion of miRNA (10%) and snRNA (25%) were identified.

Discovery of Tissue-Specific Genes in Serum

The present method also allows the detection of tissue specific genes, especially those genes specific to tissues that are difficult or even impossible to sample using biopsy. The present method for sequencing using serum provides an advantage over traditional sequencing using biopsy samples. Three tissues were selected as examples where biopsy sampling is difficult or impossible: brain, bone marrow, and peripheral nervous system (PNS). The present method was applied using three serums from three different individuals: serum A, B, and C (same as the serums described above). RNA sequencing was conducted as described in Example 2 and the data was then mapped to ENSEMBL gene annotation HG38 and matched using TiGER tool (Tissue-specific Gene Expression and Regulation, Bioinformatics Lab at Wilmer Institute, Johns Hopkins University) which provides tissue-specific gene expression profile for genes specific to certain tissues.

With the present method, when "effective" serum input volume for each serum was used (45 μL for serum A, 61 μL for serum B, and 61 μL for serum C), 176 brain specific genes, 192 bone marrow specific genes, and 78 PNS specific genes were detected in serum A; 175 brain specific genes, 191 bone marrow specific genes, and 78 PNS specific genes were detected in serum B; and 176 brain specific genes, 189 bone marrow specific genes, and 78 PNS specific genes were detected in serum C (Table 5). The total numbers of tissue specific genes for the three tissues/organs matched using TiGER tool are shown in the first row.

TABLE 5

|  | Brain Specific | Bone Marrow Specific | PNS Specific |
|---|---|---|---|
| AU in Data Base | 176 | 192 | 78 |
| Serum A | 176 | 191 | 78 |
| Serum B | 175 | 191 | 78 |
| Serum C | 176 | 189 | 78 |

FIGS. 2A-2I further show that the TPM (transcripts per million) of genes specific to these three tissues were mostly larger than 4. Success in detecting specific genes for important tissues and organs reveals the potential of applying the present method to serums as an alternative to traditional in-tissue sampling during diagnosis and prognosis of diseases related to those specific tissues or organs.

EXEMPLARY EMBODIMENTS

Exemplary embodiments provided in accordance with the presently disclosed subject matter include, but are not limited to, the claims and the following embodiments:

1. A method for detecting a plurality of ribonucleic acids (RNAs) in a biological sample from a subject, the method comprising:
(a) constructing a cDNA library from the plurality of RNAs in the biological sample, wherein an effective volume of the biological sample used to construct the cDNA library is less than or equal to about 1 mL; and
(b) detecting RNA genome equivalents in the cDNA library.

2. The method of embodiment 1, wherein the effective volume of the biological sample is less than or equal to about 500 μL.

3. The method of embodiment 1 or 2, wherein the effective volume of the biological sample is less than or equal to 250 μL.

4. The method of embodiment 1 or 2, wherein the effective volume of the biological sample is less than or equal to about 100 μL.

5. The method of any one of embodiments 1 to 4, wherein the biological sample is a cell-free biological sample.

6. The method of any one of embodiments 1 to 5, wherein at least about 100 different genes are detected.

7. The method of any one of embodiments 1 to 6, wherein at least about 1000 different genes are detected.

8. The method of any one of embodiments 1 to 7, wherein at least about 10,000 different genes are detected.

9. The method of any one of embodiments 1 to 8, wherein at least about 30,000 different genes are detected.

10. The method of any one of embodiments 1 to 9, wherein the different genes comprise different categories of RNAs.

11. The method of embodiment 10, wherein the different categories of RNAs are selected from the group consisting of mRNA, lincRNA, miRNA, snRNA, and combinations thereof.

12. The method of any one of embodiments 1 to 11, wherein the biological sample is a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample.

13. The method of embodiment 12, wherein the biological sample is a serum sample, a plasma, a saliva sample, or a cell culture media sample.

14. The method of embodiment 13, wherein the cell culture media sample is a serum sample or a plasma sample.

15. The method of embodiment 13, wherein the cell culture media sample is an in vitro fertilization (IVF) culture media sample.

16. The method of any one of embodiments 1 to 15, wherein step (a) comprises:
(a1) breaking up lipid bilayers and/or ribonucleoprotein complexes in the biological sample;
(a2) removing deoxyribonucleic acids (DNAs) in the biological sample;
(a3) synthesizing a plurality of short, double-stranded complementary DNAs (cDNAs) oligonucleotides using the RNAs in the biological sample as templates;
(a4) ligating at least one adaptor to an end of each short, double-stranded cDNA oligonucleotide to generate a plurality of adaptor-ligated, double-stranded cDNA oligonucleotides;
(a5) amplifying the plurality of adaptor-ligated, double-stranded cDNA oligonucleotides using primers that hybridize to the adaptor;
(a6) selecting one strand of each adaptor-ligated, double-stranded cDNA oligonucleotide; and
(a7) amplifying the selected strand of each adaptor-ligated, double-stranded cDNA oligonucleotide to generate the cDNA library, wherein the cDNA library comprises cDNA oligonucleotides having the same sequences as the sequences of the genomic DNAs from which the RNAs are transcribed.

17. The method of embodiment 16, wherein step (a4) comprises ligating two adaptors each to one end of each short, double-stranded cDNA oligonucleotide to generate a plurality of adaptor-ligated, double-stranded cDNA oligonucleotides.

18. The method of embodiment 17, wherein the two adaptors are the same.

19. The method of embodiment 17, wherein the two adaptors are different.

20. The method of any one of embodiments 16 to 19, wherein step (a3) comprises:
(a3.1) synthesizing a plurality of first strand cDNAs by reverse transcribing the RNAs in the biological sample;
(a3.2) fragmenting the plurality of first strand cDNAs to generate a plurality of cDNA fragments;
(a3.3) ligating a 3' primer to the 3' end of each cDNA fragment in the plurality of cDNA fragments; and
(a3.4) synthesizing the plurality of short, double-stranded cDNA oligonucleotides using a targeting primer and the plurality of cDNA fragments as templates, wherein the targeting primer comprises a first portion comprising a sequence complementary to the sequence of the 3' primer and a second portion comprising a degradable sequence.

21. The method of embodiment 20, wherein the degradable sequence comprises a uracil DNA glycosylase recognition sequence.

22. The method of embodiment 20, wherein the 3' primer is an oligonucleotide comprising identical nucleotides.

23. The method of embodiment 22, wherein the 3' primer is a poly(G) oligonucleotide, a poly(C) oligonucleotide, a poly(A) oligonucleotide, a poly(T) oligonucleotide, or a poly(U) oligonucleotide.

24. The method of embodiment 23, wherein the 3' primer is a poly(G) oligonucleotide.

25. The method of embodiment 20 or 24, wherein the sequence of the first portion is a poly(C) oligonucleotide.

26. The method of any one of embodiments 16 to 25, further comprising removing the RNAs in the biological sample.

27. The method of embodiment 26, wherein the RNAs are removed using a metal ion and/or heat shock.

28. The method of any one of embodiments 17 to 27, wherein one of the adaptors comprises a degradable sequence.

29. The method of embodiment 28, wherein the degradable sequence comprises a uracil DNA glycosylase recognition sequence.

30. The method of any one of embodiments 16 to 29, wherein the plurality of adaptor-ligated, double-stranded cDNA oligonucleotides is purified using a charge-based purification method prior to step (a5).

31. The method of embodiment 30, wherein the charge-based purification method comprises using beads.

32. The method of any one of embodiments 28 to 31, wherein in step (a6), the strand comprising the adaptor that comprises the degradable sequence is degraded.

33. The method of embodiment 32, wherein the strand is degraded by a uracil DNA glycosylase.

34. The method of any one of embodiments 16 to 33, further comprising removing cDNA oligonucleotides that encode ribosomal RNAs (rRNAs) after step (a6) and prior to step (a7).

35. The method of embodiment 34, wherein an rRNA primer is used to target the cDNA oligonucleotides encoding rRNAs.

36. The method of any one of embodiments 1 to 35, wherein step (b) comprises:
(b1) sequencing the cDNA library to detect the RNA genome equivalents.

37. The method of embodiment 36, wherein at least 10,000 sequencing reads are obtained.

38. The method of embodiment 37, wherein at least 50,000 sequencing reads are obtained.

39. The method of embodiment 38, wherein at least 1 million sequencing reads are obtained.

40. The method of any one of embodiments 36 to 39, wherein step (b) further comprises:
(b2) mapping the RNA genome equivalents detected to different categories of RNAs.

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same.

What is claimed is:

1. A method for detecting a plurality of extracellular ribonucleic acids (exRNAs) in a cell-free biological sample, wherein the biological sample is obtained from a subject or from a cell culture media, the method comprising:
   (a) constructing a cDNA library directly from the plurality of exRNAs in the biological sample, without exRNA isolation, wherein the volume of the biological sample used to construct the cDNA library is less than about 100 µL when obtained from the subject or the cell culture media; and
   (b) detecting RNA genome equivalents in the cDNA library;
   wherein step (a) comprises:
      (a3.1) producing a plurality of RNA-cDNA hybrids by reverse transcribing the exRNAs in the biological sample, wherein the RNA-cDNA hybrids include a plurality of first-strand cDNAs;
      (a3.2) fragmenting the plurality of RNA-cDNA hybrids to generate a plurality of cDNA fragments;
      (a3.3) ligating a 3' primer to the 3' end of each cDNA fragment in the plurality of cDNA fragments; and
      (a3.4) synthesizing a plurality of short, double-stranded cDNA oligonucleotides using a targeting primer and the plurality of cDNA fragments as templates, wherein the targeting primer comprises a first portion comprising a sequence complementary to the sequence of the 3' primer and a second portion comprising a degradable sequence.

2. The method of claim 1, wherein the volume of the biological sample when obtained from the subject or the cell culture media is (a) less than or equal to about 50 µL; (b) less than or equal to 25 µL; (c) less than or equal to about 10 µL; or (d) less than or equal to about 7 µL.

3. The method of claim 1, wherein (a) at least about 100 different genes are detected; (b) at least about 1000 different genes are detected; (c) at least about 10,000 different genes are detected, or (d) at least about 30,000 different genes are detected.

4. The method of claim 1, wherein the different genes comprise different categories of RNAs.

5. The method of claim 4, wherein the different categories of RNAs are selected from the group consisting of mRNA, lincRNA, miRNA, snRNA, and combinations thereof.

6. The method of claim 1, wherein the biological sample obtained from the subject is a plasma sample, a serum sample, a saliva sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample.

7. The method of claim 1, wherein the biological sample obtained from the cell culture media is a serum sample or a plasma sample or an in vitro fertilization (IVF) culture media sample.

8. The method of claim 1, wherein step (a) further comprises:
   before step (a3.1);
   (a1) breaking up lipid bilayers and/or ribonucleoprotein complexes in the biological sample; and
   (a2) removing deoxyribonucleic acids (DNAs) in the biological sample; and
   after step (a3.4):
   (a4) ligating at least one adaptor to an end of each short, double-stranded cDNA oligonucleotide to generate a plurality of adaptor-ligated, double-stranded cDNA oligonucleotides;

(a5) amplifying the plurality of adaptor-ligated, double-stranded cDNA oligonucleotides using primers that hybridize to the adaptor;

(a6) selecting one strand of each adaptor-ligated, double-stranded cDNA oligonucleotide; and (a7) amplifying the selected strand of each adaptor-ligated, double-stranded cDNA oligonucleotide to generate the cDNA library, wherein the cDNA library comprises cDNA oligonucleotides having the same sequences as the sequences of the genomic DNAs from which the RNAs are transcribed.

9. The method of claim 8, wherein step (a4) comprises ligating two adaptors each to one end of each short, double-stranded cDNA oligonucleotide to generate a plurality of adaptor-ligated, double-stranded cDNA oligonucleotides, wherein the two adaptors are the same or different.

10. The method of claim 1, wherein (a) the degradable sequence comprises a uracil DNA glycosylase recognition sequence; or (b) the 3' primer is an oligonucleotide comprising identical nucleotides; or (c) the sequence of the first portion is a poly(C) oligonucleotide.

11. The method of claim 10, wherein the 3' primer is a poly(G) oligonucleotide, a poly(C) oligonucleotide, a poly(A) oligonucleotide, a poly(T) oligonucleotide, or a poly(U) oligonucleotide.

12. The method of claim 8, further comprising removing the RNAs in the biological sample.

13. The method of claim 12, wherein the RNAs are removed using a metal ion and/or heat shock.

14. The method of claim 9, wherein one of the adaptors comprises a degradable sequence.

15. The method of claim 14, wherein the degradable sequence comprises a uracil DNA glycosylase recognition sequence.

16. The method of claim 8, wherein the plurality of adaptor ligated, double-stranded cDNA oligonucleotides are purified using a charge-based purification method prior to step (a5).

17. The method of claim 16, wherein the charge-based purification method comprises using beads.

18. The method of claim 14, wherein in step (a6), the strand comprising the adaptor that comprises the degradable sequence is degraded.

19. The method of claim 18, wherein the strand is degraded by a uracil DNA glycosylase.

20. The method of claim 8, further comprising removing cDNA oligonucleotides that encode ribosomal RNAs (rRNAs) after step (a6) and prior to step (a7).

21. The method of claim 20, wherein removing cDNA oligonucleotides that encode ribosomal RNAs (rRNAs) comprises: mixing the selected strand with an adaptor cleavage enzyme.

22. The method of claim 1, wherein step (b) comprises:
(b1) sequencing the cDNA library to detect the RNA genome equivalents.

23. The method of claim 22, wherein (i) at least 10,000 sequencing reads are obtained; (ii) at least 50,000 sequencing reads are obtained; or (iii) at least 1 million sequencing reads are obtained.

24. The method of claim 22, wherein step (b) further comprises:

(b2) mapping the RNA genome equivalents detected to different categories of RNAs.

25. The method of claim 1, wherein the biological sample is unprocessed before step (a).

26. A method for detecting a plurality of extracellular ribonucleic acids (exRNAs) in a cell-free biological sample, wherein the biological sample is obtained from a subject or from a cell culture media, the method comprising:

(a) constructing a cDNA library directly from the plurality of exRNAs in the biological sample, without exRNA isolation, wherein the volume of the biological sample used to construct the cDNA library is less than or equal to about 10 µL when obtained from the subject or the cell culture media; and (b) detecting RNA genome equivalents in the cDNA library;

wherein step (a) consists of
(a1) breaking up lipid bilayers and/or ribonucleoprotein complexes in the biological sample;
(a2) removing deoxyribonucleic acids (DNAs) in the biological sample;
(a3.1) producing a plurality of RNA-cDNA hybrids by reverse transcribing the exRNAs in the biological sample, wherein the RNA-cDNA hybrids include a plurality of first-strand cDNAs;
(a3.2) fragmenting the plurality of RNA-cDNA hybrids to generate a plurality of cDNA fragments;
(a3.3) ligating a 3' primer to the 3' end of each cDNA fragment in the plurality of cDNA fragments; and
(a3.4) synthesizing a plurality of short, double-stranded cDNA oligonucleotides using a targeting primer and the plurality of cDNA fragments as templates, wherein the targeting primer comprises a first portion comprising a sequence complementary to the sequence of the 3' primer and a second portion comprising a degradable sequence;
(a4) ligating at least one adaptor to an end of each short, double-stranded cDNA oligonucleotide to generate a plurality of adaptor-ligated, double-stranded cDNA oligonucleotides;
(a5) amplifying the plurality of adaptor-ligated, double-stranded cDNA oligonucleotides using primers that hybridize to the adaptor;
(a6) mixing the amplified adaptor-ligated, double-stranded cDNA oligonucleotides with a strand selection cocktail to obtain a selected strand comprising an adaptor that does not include a degradable sequence, the strand selection cocktail includes a rRNA depletion primer and a uracil DNA glycosylase;
(a6.1) using an adaptor cleavage enzyme to remove cDNA oligonucleotides that encode ribosomal RNAs (rRNAs); and
(a7) amplifying the selected strand of each adaptor-ligated, double-stranded cDNA oligonucleotide to generate the cDNA library, wherein the cDNA library comprises cDNA oligonucleotides having the same sequences as the sequences of the genomic DNAs from which the RNAs are transcribed.

* * * * *